United States Patent
Yeh et al.

(10) Patent No.: US 10,047,050 B2
(45) Date of Patent: Aug. 14, 2018

(54) 3,4-DI-SUBSTITUTED PYRIDINE COMPOUND, METHODS OF USING AND COMPOSITIONS COMPRISING THE SAME

(71) Applicant: ARDEA BIOSCIENCES, INC., San Diego, CA (US)

(72) Inventors: Li-Tain Yeh, Irvine, CA (US); Barry D. Quart, Encinitas, CA (US)

(73) Assignee: ARDEA BIOSCIENCES, INC., San Diego, CA (US)

( * ) Notice: Subject to any disclaimer, the term of this patent is extended or adjusted under 35 U.S.C. 154(b) by 265 days.

(21) Appl. No.: 14/355,480

(22) PCT Filed: Nov. 2, 2012

(86) PCT No.: PCT/US2012/063415
§ 371 (c)(1),
(2) Date: Apr. 30, 2014

(87) PCT Pub. No.: WO2013/067425
PCT Pub. Date: May 10, 2013

(65) Prior Publication Data
US 2014/0256748 A1    Sep. 11, 2014

Related U.S. Application Data

(60) Provisional application No. 61/616,363, filed on Mar. 27, 2012, provisional application No. 61/555,450, filed on Nov. 3, 2011.

(51) Int. Cl.
| *C07D 213/70* | (2006.01) |
| *A61K 31/44* | (2006.01) |
| *A61K 45/06* | (2006.01) |
| *A61K 31/426* | (2006.01) |
| *A61K 31/519* | (2006.01) |
| *A61K 31/4418* | (2006.01) |

(52) U.S. Cl.
CPC .......... *C07D 213/70* (2013.01); *A61K 31/426* (2013.01); *A61K 31/44* (2013.01); *A61K 31/4418* (2013.01); *A61K 31/519* (2013.01); *A61K 45/06* (2013.01)

(58) Field of Classification Search
CPC .................................................. C07D 211/72
USPC ...................................... 546/290; 514/262.1
See application file for complete search history.

(56) References Cited

U.S. PATENT DOCUMENTS

| 4,889,868 | A | 12/1989 | Huang |
| 5,614,520 | A | 3/1997 | Kondo et al. |
| 5,945,425 | A | 8/1999 | Moormann et al. |
| 6,017,925 | A | 1/2000 | Duggan |
| 7,435,752 | B2 | 10/2008 | Girardet et al. |
| 7,947,721 | B2 | 5/2011 | Girardet et al. |
| 8,003,681 | B2 | 8/2011 | Girardet et al. |
| 8,084,483 | B2 | 12/2011 | Quart et al. |
| 8,173,690 | B2 | 5/2012 | Gunic et al. |
| 8,193,234 | B2 | 6/2012 | Gunic et al. |
| 8,372,807 | B2 | 2/2013 | De La Rosa et al. |
| 8,541,589 | B2 * | 9/2013 | Ouk ..................... C07D 213/70 546/290 |
| 8,629,278 | B2 * | 1/2014 | Ouk ..................... C07D 213/70 546/290 |
| 2004/0265819 | A1 * | 12/2004 | Endou ................... C07K 14/47 435/5 |
| 2007/0099970 | A1 | 5/2007 | Mackerall et al. |
| 2007/0249686 | A1 | 10/2007 | Bonnert et al. |
| 2009/0131384 | A1 | 5/2009 | Uysal et al. |
| 2010/0016337 | A1 | 1/2010 | Strobe et al. |
| 2010/0056464 | A1 | 3/2010 | Gunic et al. |
| 2010/0137323 | A1 | 6/2010 | Brown et al. |
| 2011/0206653 | A1 * | 8/2011 | O'Neil ................ C07D 257/04 424/94.4 |
| 2012/0122780 | A1 | 5/2012 | De La Rosa et al. |
| 2013/0150381 | A1 | 6/2013 | Ouk et al. |
| 2013/0202573 | A1 | 8/2013 | Ouk et al. |

(Continued)

FOREIGN PATENT DOCUMENTS

| EP | 0513379 | 11/1992 |
| EP | 0587430 | 3/1994 |

(Continued)

OTHER PUBLICATIONS

Anzai et al, The Multivalent PDZ Domain-containing Protein PDZK1 Regulates Transport Activity of Renal Urate-Anion Exhanger URAT1 via its C Terminus, J. Biol. Chem., 279:45942-45950 (2004).
Budesinsky et al, 5-Arylpyrimidines. II. 4,6-Disubstituted 5-phenylpyrimidines, *Collection of Czechoslovak Chemical Communications*, 30/11, pp. 3730-3043, 1965.
Carroll et al, Benzylation and Benzoylation of Methyl Phenacyl Sulfone, Journal of Organic Chemistry, 30(8):2830-2 (1965).
Dewar et al., Persulphate Oxidations. Part VIII. Oxidation of Arylthio-, Arylsul-, phonyl-, and Arylamino-acetic Acids, J. Chem. Soc. Perkin Trans I, 1972, 22:2857-2861.
Emrick et al, 2-Sulfonylbiphenyls and 6,7-Dihydro-2,3,4,5-dibenzothiapin-6-one-1-dioxide;   a   Seven-Membered   Ring ß-Ketosulfone, J. Org. Chem., 1960, 25:1103-1106.
Enomoto et al, Molecular identification of a renal urate-anion exchanger that regulates blood urate levels, Nature, 417:447-451 (2002).

(Continued)

*Primary Examiner* — Timothy P Thomas
*Assistant Examiner* — George W Kosturko
(74) *Attorney, Agent, or Firm* — Wilson, Sonsini, Goodrich & Rosati

(57) ABSTRACT

2-((3-(4-cyanonaphthalen-1-yl)pyridin-4-yl)thio)-2-methylpropanoic acid is useful in the modulation of blood or serum uric acid levels. In some embodiments, 2-((3-(4-cyanonaphthalen-1-yl)pyridin-4-yl)thio)-2-methylpropanoic acid is used in the treatment or prevention of disorders related to aberrant levels of uric acid. In some embodiments, 2-((3-(4-cyanonaphthalen-1-yl)pyridin-4-yl)thio)-2-methylpropanoic acid is used for reducing serum uric acid levels in a human. Also described herein are compositions comprising 2-((3-(4-cyanonaphthalen-1-yl)pyridin-4-yl)thio)-2-methylpropanoic acid, and their use in the modulation of blood or serum uric acid levels.

13 Claims, 10 Drawing Sheets

(56) References Cited

U.S. PATENT DOCUMENTS

| | | |
|---|---|---|
| 2013/0203779 A1 | 8/2013 | Ouk et al. |
| 2013/0281469 A1 | 10/2013 | Ouk et al. |

FOREIGN PATENT DOCUMENTS

| | | |
|---|---|---|
| FR | 1381675 | 11/1964 |
| JP | 55111472 | 8/1980 |
| WO | WO 1991/016307 | 10/1991 |
| WO | WO 1995/03319 | 2/1995 |
| WO | WO 2001/91796 | 12/2001 |
| WO | WO 2002/081437 | 10/2002 |
| WO | WO 2006/026356 | 3/2006 |
| WO | WO 2006/037982 | 4/2006 |
| WO | WO 2007/050087 | 5/2007 |
| WO | WO 2009/070740 | 6/2009 |
| WO | WO 2010/028189 | 3/2010 |
| WO | WO 2010/028190 | 3/2010 |
| WO | WO 2010/135530 | 11/2010 |
| WO | WO 2010/135536 | 11/2010 |
| WO | WO 2011/044140 | 4/2011 |
| WO | WO-2011085009 A2 | 7/2011 |
| WO | WO2011/126852 | 10/2011 |
| WO | WO2011/159732 | 12/2011 |
| WO | WO2011/159839 | 12/2011 |
| WO | WO2011/159840 | 12/2011 |
| WO | WO 2011159839 A2 * | 12/2011 |

OTHER PUBLICATIONS

Janczewski et al, Synthesis of ortho- and para-biphenylylthioglycolic acids and some of their derivatives, Annals of Univsersitatis Mariae Curie-Sklodowska, 21(7):65-83 (1966) (English Abstract).

Janczewski et al, Study of Influence of molecular structure on the optical properties of compounds sulfinyl. VI. Biphenylsulfinylacetic acid, Roczniki Chemii, 35:1155-1557 (1961).

PCT/US2012/063415 International Search Report dated Jan. 2, 2013.

Shimizu et al, Syntheses and Thermal Behaviour of 9-Substituted 9-Thia-10-azaphenanthrenes, J. Chem. Soc. Perkin Trans. 1733-1747, (1991).

The Merck Index. "An encyclopedia of chemicals, drugs, and biologicals". Fourteenth Edition, 2006, p. 674 (FEBUXOSTAT).

Thomson et al, Persulphate Oxidation of Carboxylic and Sulphonic Acids and Amides, US Nat. Tech. Inform. Serv., AD Rep. (1971), 36 pgs.

* cited by examiner

3,4-DI-SUBSTITUTED PYRIDINE COMPOUND, METHODS OF USING AND COMPOSITIONS COMPRISING THE SAME

CROSS-REFERENCE

This application is filed pursuant to 35 USC 371 as a United States National Phase Application of International Application Serial No. PCT/US2012/063415, filed Nov. 2, 2012, which claims the benefit of and the right of priority to U.S. Application Ser. No. 61/555,450, filed Nov. 3, 2011, and U.S. Application Ser. No. 61/616,363, filed Mar. 27, 2012, which are hereby incorporated by reference in their entirety.

BACKGROUND OF THE INVENTION

Uric acid is the result of the oxidation of xanthine. Disorders of uric acid metabolism include, but are not limited to, polycythemia, myeloid metaplasia, gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis.

SUMMARY OF THE INVENTION

In certain embodiments, provided herein is a compound for use in reducing serum uric acid levels in a human, wherein the compound is 2-((3-(4-cyanonaphthalen-1-yl)pyridin-4-yl)thio)-2-methylpropanoic acid, or a pharmaceutically acceptable salt thereof.

In some embodiments of the compound for use, less than 100 mg per day of 2-((3-(4-cyanonaphthalen-1-yl)pyridin-4-yl)thio)-2-methylpropanoic acid, or a pharmaceutically acceptable salt thereof, is administered to the human. In certain embodiments, less than 50 mg per day of 2-((3-(4-cyanonaphthalen-1-yl)pyridin-4-yl)thio)-2-methylpropanoic acid, or a pharmaceutically acceptable salt thereof, is administered to the human. In some embodiments, about 40 mg per day of 2-((3-(4-cyanonaphthalen-1-yl)pyridin-4-yl)thio)-2-methylpropanoic acid, or a pharmaceutically acceptable salt thereof, is administered to the human. In certain embodiments, about 20 mg per day of 2-((3-(4-cyanonaphthalen-1-yl)pyridin-4-yl)thio)-2-methylpropanoic acid, or a pharmaceutically acceptable salt thereof, is administered to the human. In some embodiments, less than 20 mg per day of 2-((3-(4-cyanonaphthalen-1-yl)pyridin-4-yl)thio)-2-methylpropanoic acid, or a pharmaceutically acceptable salt thereof, is administered to the human. In certain embodiments, about 5 mg per day of 2-((3-(4-cyanonaphthalen-1-yl)pyridin-4-yl)thio)-2-methylpropanoic acid, or a pharmaceutically acceptable salt thereof, is administered to the human. In certain embodiments, less than 5 mg per day of 2-((3-(4-cyanonaphthalen-1-yl)pyridin-4-yl)thio)-2-methylpropanoic acid is administered to the human. In some embodiments, about 2 mg per day of 2-((3-(4-cyanonaphthalen-1-yl)pyridin-4-yl)thio)-2-methylpropanoic acid, or a pharmaceutically acceptable salt thereof, is administered to the human. In certain embodiments, less than 2 mg per day of 2-((3-(4-cyanonaphthalen-1-yl)pyridin-4-yl)thio)-2-methylpropanoic acid, or a pharmaceutically acceptable salt thereof, is administered to the human. In some embodiments, about 1 mg per day of 2-((3-(4-cyanonaphthalen-1-yl)pyridin-4-yl)thio)-2-methylpropanoic acid is administered to the human.

In certain embodiments of the compound for use, 24 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 0.5 mg/dL. In some embodiments, 24 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 0.8 mg/dL. In certain embodiments, 24 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 1 mg/dL. In some embodiments, 24 hours after administration of 2-((3-(4-cyanonaphthalen-1-yl)pyridin-4-yl)thio)-2-methylpropanoic acid, or a pharmaceutically acceptable salt thereof, the serum uric acids levels are reduced by at least 2 mg/dL. In certain embodiments, 24 hours after administration of 2-((3-(4-cyanonaphthalen-1-yl)pyridin-4-yl)thio)-2-methylpropanoic acid, or a pharmaceutically acceptable salt thereof, the serum uric acids levels are reduced by at least 3 mg/dL.

In some embodiments, 48 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 0.5 mg/dL. In certain embodiments, 48 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 1 mg/dL. In some embodiments, 48 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 3 mg/dL.

In certain embodiments, 72 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 0.5 mg/dL. In some embodiments, 72 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 1 mg/dL. In certain embodiments, 72 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by about 2 mg/dL.

In some embodiments of the compound for use, 24 hours after administration of 2-((3-(4-cyanonaphthalen-1-yl)pyridin-4-yl)thio)-2-methylpropanoic acid, the serum uric acid levels are reduced by at least 15% from baseline. In certain embodiments, 24 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 20% from baseline. In some embodiments, 24 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 30% from baseline. In certain embodiments, 24 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 40% from baseline. In some embodiments, 24 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by about 20% from baseline. In certain embodiments, 24 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by about 40% from baseline. In some embodiments, 24 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by about 60% from baseline.

In certain embodiments, 48 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by about 10% from baseline. In some embodiments, 48 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 20% from baseline. In certain embodiments, 48 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 30% from baseline. In some embodiments, 48 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by about 40% from baseline. In certain embodiments, 48 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by about 50% from baseline. In some embodiments, 72 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 15% from baseline. In certain embodiments, 72 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 20% from baseline. In some embodiments, 72 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by about 20% from baseline. In certain embodiments, 72 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by about 30% from baseline.

In certain embodiments, the compound is for use in treating or preventing a condition characterized by abnormal tissue or organ levels of uric acid. In some embodiments, the condition is gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis, sarcoidosis, hypoxanthine-guanine phosphoribosyltransferase (HPRT) deficiency or a combination thereof. In specific embodiments, the condition is gout.

In certain embodiments of the compound for use, a second agent effective for the treatment of the gout is administered to the human. In some embodiments, the second agent is a URAT 1 inhibitor, a xanthine oxidase inhibitor, a xanthine dehydrogenase, a xanthine oxidoreductase inhibitor, or combinations thereof. In certain embodiments, the URAT 1 inhibitor is 2-((5-bromo-4-(4-cyclopropyl-1-naphthalenyl)-4H-1,2,4-triazol-3-yl)thio)acetic acid, or a pharmaceutically acceptable salt thereof. In some embodiments, the xanthine oxidase inhibitor is allopurinol or febuxostat.

In certain embodiments, provided herein are methods of reducing serum uric acid levels in a human, comprising administering 2-((3-(4-cyanonaphthalen-1-yl)pyridin-4-yl)thio)-2-methylpropanoic acid, or a pharmaceutically acceptable salt thereof, to the human.

In some embodiments, the method comprises administering less than 100 mg, less than 50 mg per day, about 40 mg per day, about 20 mg per day, less than 20 mg per day, about 5 mg per day, less than 5 mg per day, about 2 mg per day, less than 2 mg per day, or about 1 mg per day of 2-((3-(4-cyanonaphthalen-1-yl)pyridin-4-yl)thio)-2-methylpropanoic acid or a pharmaceutically acceptable salt thereof.

In some embodiments, the serum uric acid levels are reduced by at least 0.5 mg/dL, at least 0.8 mg/dL, at least 1 mg/dL, at least 2 mg/dL, or at least 3 mg/dL 24 hours after administration of 2-((3-(4-cyanonaphthalen-1-yl)pyridin-4-yl)thio)-2-methylpropanoic acid, or a pharmaceutically acceptable salt thereof. In certain embodiments, the serum uric acid levels are reduced by at least 0.5 mg/dL, at least 1 mg/dL, or at least 3 mg/dL 48 hours after administration of 2-((3-(4-cyanonaphthalen-1-yl)pyridin-4-yl)thio)-2-methylpropanoic acid, or a pharmaceutically acceptable salt thereof. In certain embodiments, the serum uric acid levels are reduced by at least 0.5 mg/dL, at least 1 mg/dL, or 2 mg/dL 72 hours after administration of 2-((3-(4-cyanonaphthalen-1-yl)pyridin-4-yl)thio)-2-methylpropanoic acid, or a pharmaceutically acceptable salt thereof.

In some embodiments, the serum uric acid levels are reduced by at least 15% from baseline, at least 20% from baseline, at least 30% from baseline, at least 40% from baseline, about 20% from baseline, or about 40% from baseline, about 60% from baseline 24 hours after administration of 2-((3-(4-cyanonaphthalen-1-yl)pyridin-4-yl)thio)-2-methylpropanoic acid, or a pharmaceutically acceptable salt thereof. In some embodiments, the serum uric acid levels are reduced by about 10% from baseline, at least 20% from baseline, at least 30% from baseline, about 40% from baseline, or about 50% from baseline 48 hours after administration of 2-((3-(4-cyanonaphthalen-1-yl)pyridin-4-yl)thio)-2-methylpropanoic acid, of a pharmaceutically acceptable salt thereof. In certain embodiments, the serum uric acid levels are reduced by at least 15% from baseline, at least 20% from baseline, about 20% from baseline, or about 30% from baseline 72 hours after administration of 2-((3-(4-cyanonaphthalen-1-yl)pyridin-4-yl)thio)-2-methylpropanoic acid, or a pharmaceutically acceptable salt thereof.

In some embodiments, the method is for treating or preventing a condition characterized by abnormal tissue or organ levels of uric acid. In certain embodiments, the condition is gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis, sarcoidosis, hypoxanthine-guanine phosphoribosyltransferase (HPRT) deficiency or a combination thereof. In specific embodiments, the condition is gout.

In certain embodiments, the methods further comprise administering a second agent effective for the treatment of the gout. In some embodiments, the second agent is a URAT 1 inhibitor, a xanthine oxidase inhibitor, a xanthine dehydrogenase, a xanthine oxidoreductase inhibitor, or combinations thereof. In certain embodiments, the URAT 1 inhibitor is 2-((5-bromo-4-(4-cyclopropyl-1-naphthalenyl)-4H-1,2,4-triazol-3-yl)thio)acetic acid, or a pharmaceutically acceptable salt or ester thereof. In some embodiments, the xanthine oxidase inhibitor is allopurinol or febuxostat.

In certain embodiments, provided herein is a use of a compound in the manufacture of a medicament for reducing serum uric acid levels in a human, wherein the compound is 2-((3-(4-cyanonaphthalen-1-yl)pyridin-4-yl)thio)-2-methylpropanoic acid, or a pharmaceutically acceptable salt thereof.

In some embodiments of the use of a compound in the manufacture of a medicament, less than 100 mg per day, less than 50 mg per day, about 40 mg per day, about 20 mg per day, less than 20 mg per day, about 5 mg per day, less than 5 mg per day, about 2 mg per day, less than 2 mg per day, or about 1 mg per day of 2-((3-(4-cyanonaphthalen-1-yl)pyridin-4-yl)thio)-2-methylpropanoic acid is administered to the human.

In certain embodiments of the use of a compound in the manufacture of a medicament, 24 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 0.5 mg/dL, at least 0.8 mg/dL, at least 1 mg/dL, at least 2 mg/dL, or at least 3 mg/dL. In some embodiments, 48 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 0.5 mg/dL, at least 1 mg/dL, or at least 3 mg/dL. In certain embodiments, 72 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 0.5 mg/dL, at least 1 mg/dL, or about 2 mg/dL.

In some embodiments of the use of a compound in the manufacture of a medicament, 24 hours after administration of 2-((3-(4-cyanonaphthalen-1-yl)pyridin-4-yl)thio)-2-methylpropanoic acid, the serum uric acid levels are reduced by at least 15% from baseline, at least 20% from baseline, at least 30% from baseline, at least 40% from baseline, about 20% from baseline, about 40% from baseline, or about 60% from baseline. In certain embodiments, 48 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by about 10% from baseline, at least 20% from baseline, at least 30% from baseline, about 40% from baseline, or about 50% from baseline. In some embodiments, 72 hours after administration of 2-((3-(4-cyanonaphthalen-1-yl)pyridin-4-yl)thio)-2-methylpropanoic acid, or a pharmaceutically acceptable salt thereof, the serum uric acid levels are reduced by at least 15% from baseline, at least 20% from baseline, about 20% from baseline, or about 30% from baseline.

In certain embodiments of the use of a compound in the manufacture of a medicament, the medicament is for use in treating or preventing a condition characterized by abnormal tissue or organ levels of uric acid. In some embodiments, the condition is gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis, sarcoidosis, hypoxanthine-guanine phosphoribosyltransferase (HPRT) deficiency or a combination thereof. In specific embodiments, the condition is gout.

In certain embodiments of the use of a compound in the manufacture of a medicament, the medicament is administered with a second agent effective for the treatment of the gout. In some embodiments, the second agent is a URAT 1 inhibitor, a xanthine oxidase inhibitor, a xanthine dehydrogenase, a xanthine oxidoreductase inhibitor, or combinations thereof. In certain embodiments, the URAT 1 inhibitor is 2-((5-bromo-4-(4-cyclopropyl-1-naphthalenyl)-4H-1,2,4-triazol-3-yl)thio)acetic acid, or a pharmaceutically acceptable salt or ester thereof. In some embodiments, the xanthine oxidase inhibitor is allopurinol or febuxostat.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
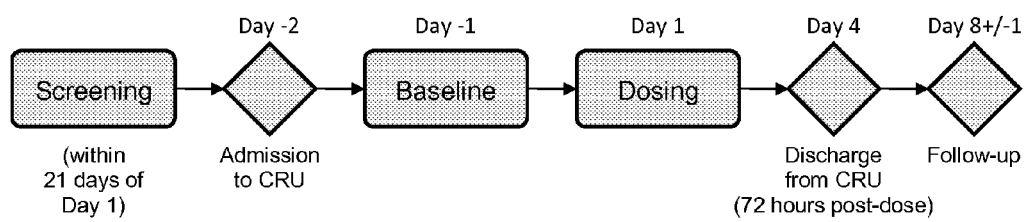
FIG. 1A shows a schematic representation of schedule of events during the trial described in Example 3.

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The section headings used herein are for organizational purposes only and are not to be construed as limiting the subject matter described.

Certain Pharmaceutical Terminology

The term "patient", "subject" or "individual" are used interchangeably. As used herein, they refer to individuals suffering from a disorder, and the like, encompasses mammals and non-mammals. None of the terms require that the individual be under the care and/or supervision of a medical professional. Mammals are any member of the Mammalian class, including but not limited to, humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the individual is a mammal. In preferred embodiments, the individual is a human.

The terms "treat," "treating" or "treatment," and other grammatical equivalents as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The term "about" generally refers to a range of numbers that one of skill in the art would consider equivalent to the recited value (e.g., having the same function or result). In many instances, the term "about" may include numbers that are rounded to the nearest significant figure. In preferred instances, the term "about" means within 10% of a given value or range.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In preferred embodiments, the compounds and compositions described herein are administered orally.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising 2-((3-(4-cyanonaphthalen-1-yl)pyridin-4-yl)thio)-2-methylpropanoic acid required to provide a clinically significant decrease in a disease. An appropriate "effective" amount may differ from one individual to another. An appropriate "effective" amount in any individual case may be determined using techniques, such as a dose escalation study.

The term "acceptable" as used herein, with respect to a formulation, composition or ingredient, means having no persistent detrimental effect on the general health of the individual being treated.

The term "pharmaceutically acceptable" as used herein, refers to a material, such as a carrier or diluent, which does not abrogate the biological activity or properties of 2-((3-(4-cyanonaphthalen-1-yl)pyridin-4-yl)thio)-2-methylpropanoic acid, and is relatively nontoxic, i.e., the material may be administered to an individual without causing undesirable biological effects or interacting in a deleterious manner with any of the components of the composition in which it is contained.

The term "prodrug" as used herein, refers to a drug precursor that, following administration to an individual and subsequent absorption, is converted to an active, or a more active species via some process, such as conversion by a metabolic pathway. Thus, the term encompasses any derivative of 2-((3-(4-cyanonaphthalen-1-yl)pyridin-4-yl)thio)-2-methylpropanoic acid, which, upon administration to a recipient, is capable of providing, either directly or indirectly, 2-((3-(4-cyanonaphthalen-1-yl)pyridin-4-yl)thio)-2-methylpropanoic acid or a pharmaceutically active metabolite or residue thereof. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. They may, for instance, be bioavailable by oral administration whereas the parent is not. Particularly favored derivatives or prodrugs are those that increase the bioavailability of 2-((3-(4-cyanonaphthalen-1-yl)pyridin-4-yl)thio)-2-methylpropanoic acid when administered to an individual (e.g. by allowing an orally administered compound to be more readily absorbed into the blood) or which enhance delivery of the parent compound to a biological compartment (e.g. the brain or lymphatic system).

The term "pharmaceutically acceptable salt" as used herein, refers to salts that retain the biological effectiveness of the free acids and bases of 2-((3-(4-cyanonaphthalen-1-yl)pyridin-4-yl)thio)-2-methylpropanoic acid and that are not biologically or otherwise undesirable. 2-((3-(4-cyanonaphthalen-1-yl)pyridin-4-yl)thio)-2-methylpropanoic acid may react with inorganic or organic bases, and inorganic and organic acids, to form a pharmaceutically acceptable salt. These salts can be prepared in situ during the final isolation and purification, or by separately reacting the purified compound in its free base form with a suitable organic or inorganic acid, and isolating the salt thus formed.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, excipients and the like.

The term "carrier" as used herein, refers to relatively nontoxic chemical compounds or agents that facilitate the incorporation of a compound into cells or tissues.

The terms "pharmaceutical combination", "administering an additional therapy", "administering an additional therapeutic agent" and the like, as used herein, refer to a pharmaceutical therapy resulting from the mixing or combining of more than one active ingredient and includes both fixed and non-fixed combinations of the active ingredients. The term "fixed combination" means that 2-((3-(4-cyanonaphthalen-1-yl)pyridin-4-yl)thio)-2-methylpropanoic acid, and at least one co-agent, are both administered to an individual simultaneously in the form of a single entity or dosage. The term "non-fixed combination" means that 2-((3-(4-cyanonaphthalen-1-yl)pyridin-4-yl)thio)-2-methylpropanoic acid, and at least one co-agent, are administered to an individual as separate entities either simultaneously, concurrently or sequentially with variable intervening time limits, wherein such administration provides effective levels of the two or more compounds in the body of the individual. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single individual, and are intended to include treatment regimens in which the agents are administered by the same or different route of administration or at the same or different times. In some embodiments 2-((3-(4-cyanonaphthalen-1-yl)pyridin-4-yl)thio)-2-methylpropanoic acid will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, 2-((3-(4-cyanonaphthalen-1-yl)pyridin-4-yl)thio)-2-methylpropanoic acid and the other agent(s) are administered in a single composition. In some embodiments, 2-((3-(4-cyanonaphthalen-1-yl)pyridin-4-yl)thio)-2-methylpropanoic acid and the other agent(s) are admixed in the composition.

The term "metabolite," as used herein, refers to a derivative of 2-((3-(4-cyanonaphthalen-1-yl)pyridin-4-yl)thio)-2-methylpropanoic acid formed when the compound is metabolized.

The term "active metabolite," as used herein, refers to a biologically active derivative of 2-((3-(4-cyanonaphthalen-1-yl)pyridin-4-yl)thio)-2-methylpropanoic acid formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Further information on metabolism may be obtained from *The Pharmacological Basis of Therapeutics*, 9th Edition, McGraw-Hill (1996).

Modes of Administration

In some embodiments, 2-((3-(4-cyanonaphthalen-1-yl)pyridin-4-yl)thio)-2-methylpropanoic acid is administered either alone or in combination with pharmaceutically acceptable carriers, excipients or diluents, in a pharmaceutical composition. Administration can be effected by any method that enables delivery of 2-((3-(4-cyanonaphthalen-1-yl)pyridin-4-yl)thio)-2-methylpropanoic acid to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, 2-((3-(4-cyanonaphthalen-1-yl)pyridin-4-yl)thio)-2-methylpropanoic acid can be administered locally to the area in need of treatment, by for example, local infusion during surgery, topical application such as creams or ointments, injection, catheter, or implant, said implant made for example, out of a porous, non-porous, or gelatinous material, including membranes, such as silastic membranes, or fibers. The administration can also be by direct injection at the site of a diseased tissue or organ.

In some embodiments, formulations suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical preparations that can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical preparations are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of 2-((3-(4-cyanonaphthalen-1-yl)pyridin-4-yl)thio)-2-methylpropanoic acid to allow for the preparation of highly concentrated solutions.

Pharmaceutical preparations may also be formulated as a depot preparation. Such long acting formulations may be administered by implantation (for example subcutaneously or intramuscularly) or by intramuscular injection. Thus, for example, 2-((3-(4-cyanonaphthalen-1-yl)pyridin-4-yl)thio)-2-methylpropanoic acid may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical preparations may also be formulated in rectal compositions such as suppositories or retention enemas, e.g., containing conventional suppository bases such as cocoa butter, polyethylene glycol, or other glycerides.

Pharmaceutical preparations may be administered topically, that is by non-systemic administration. This includes the application of 2-((3-(4-cyanonaphthalen-1-yl)pyridin-4-yl)thio)-2-methylpropanoic acid externally to the epidermis or the buccal cavity and the instillation into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Pharmaceutical preparations for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix with a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, 2-((3-(4-cyanonaphthalen-1-yl)pyridin-4-yl)thio)-2-methylpropanoic acid may include other agents conventional in the art having regard to the type of formulation in question, for example those suitable for oral administration may include flavoring agents.

Formulations 2-((3-(4-Cyanonaphthalen-1-yl)pyridin-4-yl)thio)-2-methylpropanoic acid can be delivered in a vesicle, such as a liposome. 2-((3-(4-Cyanonaphthalen-1-yl)pyridin-4-yl)thio)-2-methylpropanoic acid can also be delivered in a controlled release system, or a controlled release system can be placed in proximity of the therapeutic target. In one embodiment, a pump may be used.

The pharmaceutical compositions described herein can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use are optionally prepared according to known method, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium croscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration 2-((3-(4-cyanonaphthalen-1-yl)pyridin-4-yl)thio)-2-methylpropanoic acid may be combined with various sweetening or flavoring agents, coloring matters or dyes and, if desired, emulsifying agents or suspending agents, together with diluents such as water, ethanol, propylene glycol, glycerin, or combinations thereof.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

Pharmaceutical compositions may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

Pharmaceutical compositions may be in the form of a sterile injectable aqueous solution. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion. The injectable solutions or microemulsions may be introduced into an individual's blood-stream by local bolus injection. Alternatively, it may be advantageous to administer the solution or microemulsion in such a way as to maintain a constant circulating concentration of 2-((3-(4-cyanonaphthalen-1-yl)pyridin-4-yl)thio)-2-methylpropanoic acid. In order to maintain such a constant concentration, a continuous intravenous delivery device may be utilized. An example of such a device is the Deltec CADD-PLUS™ model 5400 intravenous pump. The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutical compositions may also be administered in the form of suppositories for rectal administration of the drug. These compositions can be prepared by mixing the active ingredient with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing 2-((3-(4-cyanonaphthalen-1-yl)pyridin-4-yl)thio)-2-methylpropanoic acid can be used. As used herein, topical application can include mouth washes and gargles.

Pharmaceutical compositions may be administered in intranasal form via topical use of suitable intranasal vehicles and delivery devices, or via transdermal routes, using transdermal skin patches. To be administered in the form of a transdermal delivery system, the dosage administration will, of course, be continuous rather than intermittent throughout the dosage regimen.

The formulations may conveniently be presented in unit dosage form and may be prepared by any of the methods well known in the art of pharmacy. All methods include the step of bringing into association 2-((3-(4-cyanonaphthalen-1-yl)pyridin-4-yl)thio)-2-methylpropanoic acid or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Dosage Forms

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition may include a conventional pharmaceutical carrier or excipient and 2-((3-(4-cyanonaphthalen-1-yl)pyridin-4-yl)thio)-2-methylpropanoic acid as an active ingredient. In addition, it may include other medicinal or pharmaceutical agents, carriers, adjuvants, etc.

Exemplary parenteral administration forms include solutions or suspensions of 2-((3-(4-cyanonaphthalen-1-yl)pyridin-4-yl)thio)-2-methylpropanoic acid in sterile aqueous solutions, for example, aqueous propylene glycol or dextrose solutions. Such dosage forms can be suitably buffered, if desired.

Doses

The amount of pharmaceutical composition administered will firstly be dependent on the mammal being treated. In the instances where pharmaceutical compositions are administered to a human individual, the daily dosage will normally be determined by the prescribing physician with the dosage generally varying according to the age, sex, diet, weight, general health and response of the individual, the severity of the individual's symptoms, the precise indication or condition being treated, the severity of the indication or condition being treated, time of administration, route of administration, the disposition of the composition, rate of excretion, drug combination, and the discretion of the prescribing physician. Also, the route of administration may vary depending on the condition and its severity. Preferably, the pharmaceutical composition is in unit dosage form. In such form, the preparation is subdivided into unit doses containing appropriate quantities of the active component, e.g., an effective amount to achieve the desired purpose. Determination of the proper dosage for a particular situation is within the skill of the art. In some instances, treatment may be initiated with smaller dosages which are less than the optimum dose of 2-((3-(4-cyanonaphthalen-1-yl)pyridin-4-yl)thio)-2-methylpropanoic acid. Thereafter, the dosage is increased by small amounts until the optimum effect under the circumstances is reached. For convenience, the total daily dosage may be divided and administered in portions during the day if desired. The amount and frequency of administration of 2-((3-(4-cyanonaphthalen-1-yl)pyridin-4-yl)thio)-2-methylpropanoic acid, and if applicable other therapeutic agents and/or therapies, will be regulated according to the judgment of the attending clinician (physician) considering such factors as described above. Thus the amount of pharmaceutical composition to be administered may vary widely.

Administration may occur in an amount of less than about 50 mg/kg of body weight per day (administered in single or divided doses). A particular therapeutic dosage can include, e.g., less than about 1000 mg of 2-((3-(4-cyanonaphthalen-1-yl)pyridin-4-yl)thio)-2-methylpropanoic acid, and preferably includes, e.g., less than about 250 mg. The quantity of 2-((3-(4-cyanonaphthalen-1-yl)pyridin-4-yl)thio)-2-methylpropanoic acid in a unit dose of preparation may be varied or adjusted from less than about 500 mg, preferably from less than about 100 mg, more preferably from less than about 50 mg, or from less than 5 mg, according to the particular application. In some instances, dosage levels below the lower limit of the aforesaid range may be more than adequate, while in other cases still larger doses may be employed without causing any harmful side effect, e.g. by dividing such larger doses into several small doses for administration throughout the day. In combinational applications in which 2-((3-(4-cyanonaphthalen-1-yl)pyridin-4-yl)thio)-2-methylpropanoic acid is not the sole therapy, it may be possible to administer lesser amounts and still have therapeutic or prophylactic effect.

In some embodiments, 2-((3-(4-cyanonaphthalen-1-yl)pyridin-4-yl)thio)-2-methylpropanoic acid is administered once a day. In other embodiments, 2-((3-(4-cyanonaphthalen-1-yl)pyridin-4-yl)thio)-2-methylpropanoic acid is administered twice a day. In some embodiments, 2-((3-(4-cyanonaphthalen-1-yl)pyridin-4-yl)thio)-2-methylpropanoic acid is administered with food. In other embodiments, 2-((3-(4-cyanonaphthalen-1-yl)pyridin-4-yl)thio)-2-methylpropanoic acid is administered without food.

The therapeutic dosing of 2-((3-(4-cyanonaphthalen-1-yl)pyridin-4-yl)thio)-2-methylpropanoic acid described in the section entitled "Methods of Reducing Serum Uric Acid Levels" and the examples may be used to treat any of the diseases described herein.

Combination Therapies 2-((3-(4-cyanonaphthalen-1-yl)pyridin-4-yl)thio)-2-methylpropanoic acid or a pharmaceutically acceptable salt, solvate, polymorph, ester, tautomer or prodrug thereof may be administered as a sole therapy, or in combination with another therapy or therapies.

For example, therapeutic effectiveness may be enhanced by administration of an adjuvant (i.e., by itself the adjuvant may only have minimal therapeutic benefit, but in combination with another therapeutic agent, the overall therapeutic benefit to the individual is enhanced). Or, by way of example only, the benefit experienced by an individual may be increased by administering 2-((3-(4-cyanonaphthalen-1-yl)pyridin-4-yl)thio)-2-methylpropanoic acid with another therapeutic agent (which also includes a therapeutic regimen) that also has therapeutic benefit. By way of example only, in a treatment for gout, increased therapeutic benefit may result by also providing the individual with another therapeutic agent for gout. Or, the additional therapy or therapies may include, but are not limited to physiotherapy, psychotherapy, radiation therapy, application of compresses to a diseased area, rest, altered diet, and the like. Regardless of the disease, disorder or condition being treated, the overall benefit experienced by the individual may be additive of the two therapies or therapeutic agents or the individual may experience a synergistic benefit.

In the instances where 2-((3-(4-cyanonaphthalen-1-yl)pyridin-4-yl)thio)-2-methylpropanoic acid is administered in combination with other therapeutic agents, 2-((3-(4-cyanonaphthalen-1-yl)pyridin-4-yl)thio)-2-methylpropanoic acid need not be administered in the same pharmaceutical composition as other therapeutic agents, and may, because of different physical and chemical characteristics, be administered by a different route. For example, 2-((3-(4-cyanonaphthalen-1-yl)pyridin-4-yl)thio)-2-methylpropanoic acid may be administered orally to generate and maintain good blood levels thereof, while the other therapeutic agent may be administered intravenously. Thus 2-((3-(4-cyanonaphthalen-1-yl)pyridin-4-yl)thio)-2-methylpropanoic acid may be administered concurrently (e.g., simultaneously, essentially simultaneously or within the same treatment protocol), sequentially or dosed separately to other therapeutic agents. The initial administration can be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. In some embodiments, the additional agent is a URAT 1 inhibitor, a xanthine oxidase inhibitor, a xanthine dehydrogenase, a xanthine oxidoreductase inhibitor, a purine nucleoside phosphorylase (PNP) inhibitor, a uric acid transporter inhibitor, a glucose transporter (GLUT) inhibitor, a GLUT-9 inhibitor, a solute carrier family 2 (facilitated glucose transporter), member 9 (SLC2A9) inhibitor, an organic anion transporter (OAT) inhibitor, an OAT-4 inhibitor, or combinations thereof. In certain instances, URAT 1 is an ion exchanger that mediates urate transportation. In certain instances, URAT I mediates urate transportation in the proximal tubule. In certain instances, URAT I exchanges urate in a proximal tubule for lactate and nicotinate. In certain instances, xanthine oxidase oxidizes hypoxanthine to xanthine, and further to uric acid. In certain instances, xanthine dehydrogenase catalyzes the conversion of xanthine, $NAD^+$, and $H_2O$ into urate, NADH, and $H^+$. In some embodiments, the additional agent is 2-((5-bromo-4-(4-cyclopropyl-1-naphthalenyl)-4H-1,2,4-triazol-3-yl)thio)acetic acid, allopurinol, febuxostat (2-(3-cyano-4-isobutoxyphenyl)-4-methyl-1,3-thiazole-5-carboxylic acid), FYX-051 (4-(5-pyridin-4-yl-1H-[1,2,4]triazol-3-yl)pyridine-2-carbonitrile), probenecid, sulfinpyrazone, benzbromarone, acetaminophen, steroids, nonsteroidal anti-inflammatory drugs (NSAIDs), adrenocorticotropic hormone (ACTH), colchicine, a glucorticoid, an adrogen, a cox-2 inhibitor, a PPAR agonist, naproxen, sevelamer, sibutmaine, troglitazone, proglitazone, another uric acid lowering agent, losartan, fibric acid, benziodarone, salicylate, anlodipine, vitamin C, or combinations thereof.

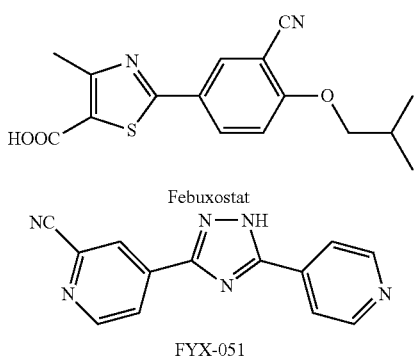

Febuxostat

FYX-051

Diseases

Described herein are methods of treating a disease in an individual suffering from said disease comprising administering to said individual an effective amount of 2-((3-(4-cyanonaphthalen-1-yl)pyridin-4-yl)thio)-2-methylpropanoic acid or a pharmaceutically acceptable salt, solvate, polymorph, ester, tautomer or prodrug thereof.

Also described herein are methods of preventing or delaying onset of a disease in an individual at risk for developing said disease comprising administering to said individual an effective amount to prevent or delay onset of said disease, of a composition comprising 2-((3-(4-cyanonaphthalen-1-yl)pyridin-4-yl)thio)-2-methylpropanoic acid or a pharmaceutically acceptable salt, solvate, polymorph, ester, tautomer or prodrug thereof.

Further described herein are methods for the prophylaxis or treatment of any disease or disorder in which aberrant levels of uric acid plays a role including, without limitation: hyperuricemia, gout, gouty arthritis, inflammatory arthritis, kidney disease, nephrolithiasis (kidney stones), joint inflammation, deposition of urate crystals in joints, urolithiasis (formation of calculus in the urinary tract), deposition of urate crystals in renal parenchyma, Lesch-Nyhan syndrome, Kelley-Seegmiller syndrome, gout flare, tophaceous gout, kidney failure, or combinations thereof in a human or other mammal. The methods disclosed herein extend to such a use and to the use of 2-((3-(4-cyanonaphthalen-1-yl)pyridin-4-yl)thio)-2-methylpropanoic acid for the manufacture of a medicament for treating such diseases or disorders. Further, the methods disclosed herein extend to the administration to a human an effective amount of 2-((3-(4-cyanonaphthalen-1-yl)pyridin-4-yl)thio)-2-methylpropanoic acid for treating any such disease or disorder.

Individuals that can be treated with 2-((3-(4-cyanonaphthalen-1-yl)pyridin-4-yl)thio)-2-methylpropanoic acid, or a pharmaceutically acceptable salt, ester, prodrug, solvate, hydrate or derivative thereof, according to the methods of this invention include, for example, individuals that have been diagnosed as having gout, gouty arthritis, inflammatory arthritis, kidney disease, nephrolithiasis (kidney stones), joint inflammation, deposition of urate crystals in joints, urolithiasis (formation of calculus in the urinary tract), deposition of urate crystals in renal parenchyma, Lesch-Nyhan syndrome, Kelley-Seegmiller syndrome, gout flare, tophaceous gout, kidney failure, or combinations thereof.

In some embodiments, an individual having an aberrant uric acid level is administered an amount of 2-((3-(4-cyanonaphthalen-1-yl)pyridin-4-yl)thio)-2-methylpropanoic acid sufficient to modulate the aberrant uric acid level (e.g., to a medically-acceptable level). In some embodiments, an individual treated with t2-((3-(4-cyanonaphthalen-1-yl)pyridin-4-yl)thio)-2-methylpropanoic acid displays aberrant uric acid levels wherein the uric acid levels in blood exceed a medically-accepted range (i.e., hyperuricemia). In some embodiments, an individual treated with 2-((3-(4-cyanonaphthalen-1-yl)pyridin-4-yl)thio)-2-methylpropanoic acid displays aberrant uric acid levels wherein uric acid levels in the blood exceed 360 μmmol/L (6 mg/dL) for a female individual or 400 μmmol/L (6.8 mg/dL) for a male individual. In some embodiments, an individual treated with 2-((3-(4-cyanonaphthalen-1-yl)pyridin-4-yl)thio)-2-methylpropanoic acid displays aberrant uric acid levels wherein uric acid levels in urine exceed a medically-accepted range (i.e., hyperuricosuria). In some embodiments, an individual treated with 2-((3-(4-cyanonaphthalen-1-yl)pyridin-4-yl)thio)-2-methylpropanoic acid displays aberrant uric acid levels wherein uric acid levels in urine exceed 800 mg/day (in a male individual) and greater than 750 mg/day (in a female individual).

In some embodiments, an individual treated with 2-((3-(4-cyanonaphthalen-1-yl)pyridin-4-yl)thio)-2-methylpropanoic acid (1) displays aberrant uric acid levels, and (2) suffers from a cardiovascular disorder. In some embodiments, an individual treated with 2-((3-(4-cyanonaphthalen-1-yl)pyridin-4-yl)thio)-2-methylpropanoic acid (1) displays aberrant uric acid levels, and (2) suffers from an aneurysm; angina; atherosclerosis; a stroke; cerebrovascular disease; congestive heart failure; coronary artery disease; and/or a myocardial infarction. In some embodiments, an individual treated with 2-((3-(4-cyanonaphthalen-1-yl)pyridin-4-yl)thio)-2-methylpropanoic acid (1) displays aberrant uric acid levels, and (2) displays (a) c-reactive protein (CRP) levels above about 3.0 mg/L; (b) homocysteine levels above about 15.9 mmol/L; (c) LDL levels above about 160 mg/dL; (d) HDL levels below about 40 mg/dL; and/or (e) serum creatinine levels above about 1.5 mg/dL.

In some embodiments, an individual treated with 2-((3-(4-cyanonaphthalen-1-yl)pyridin-4-yl)thio)-2-methylpropanoic acid (1) displays aberrant uric acid levels, and (2) suffers from diabetes. In some embodiments, an individual treated with 2-((3-(4-cyanonaphthalen-1-yl) pyridin-4-yl thio)-2-methylpropanoic acid (1) displays aberrant uric acid levels, and (2) suffers from Type I diabetes. In some embodiments, an individual treated with 2-((3-(4-cyanonaphthalen-1-yl) pyridin-4-yl thio)-2-methylpropanoic acid (1) displays aberrant uric acid levels, and (2) suffers from Type II diabetes. In some embodiments, an individual treated with 2-((3-(4-cyanonaphthalen-1-yl) pyridin-4-yl thio)-2-methylpropanoic acid (1) displays aberrant uric acid levels, and (2) suffers from a loss of beta cells of the islets of Langerhans in the pancreas. In some embodiments, an individual treated with 2-((3-(4-cyanonaphthalen-1-yl) pyridin-4-yl thio)-2-methylpropanoic acid (1) displays aberrant uric acid levels, and (2) suffers from insulin resistance and/or reduced insulin sensitivity. In some embodiments, an individual treated with 2-((3-(4-cyanonaphthalen-1-yl) pyridin-4-yl thio)-2-methylpropanoic acid (1) displays aberrant uric acid levels, and (2) displays (a) a fasting plasma glucose level ≥126 mg/dL; (b) a plasma glucose level ≥200 mg/dL two hours after a glucose tolerance test; and/or (c) symptoms of hyperglycemia and casual plasma glucose levels ≥200 mg/dL (11.1 mmol/l).

In some embodiments, an individual treated with 2-((3-(4-cyanonaphthalen-1-yl) pyridin-4-yl thio)-2-methylpropanoic acid (1) displays aberrant uric acid levels, and (2) suffers from metabolic syndrome. In some embodiments, an individual treated with 2-((3-(4-cyanonaphthalen-1-yl) pyridin-4-yl thio)-2-methylpropanoic acid (1) displays aberrant uric acid levels, and (2) suffers from (a) diabetes mellitus, impaired glucose tolerance, impaired fasting glucose and/or insulin resistance, (b) at least two of (i) blood pressure: ≥140/90 mmHg; (ii) dyslipidaemia: triglycerides (TG): ≥1.695 mmol/L and high-density lipoprotein cholesterol (HDL-C)≤0.9 mmol/L (male), ≤1.0 mmol/L (female); (iii) central obesity:waist:hip ratio >0.90 (male); >0.85 (female), and/or body mass index >30 kg/m2; and (iv) microalbuminuria: urinary albumin excretion ratio≥20 mg/min or albumin:creatinine ratio≥30 mg/g. In some embodiments, an individual treated with 2-((3-(4-cyanonaphthalen-1-yl) pyridin-4-yl thio)-2-methylpropanoic acid (1) displays aberrant uric acid levels, and (2) suffers from insulin resistance (i.e., the top 25% of the fasting insulin values among non-diabetic individuals) and (b) at least two of (i) central obesity: waist circumference ≥94 cm (male), ≥80 cm (female); (ii) dyslipidaemia: TG≥2.0 mmol/L and/or HDL-C<1.0 mmol/L or treated for dyslipidaemia; (iii) hypertension: blood pressure ≥140/90 mmHg or antihypertensive medication; and (iv) fasting plasma glucose ≥6.1 mmol/L. In some embodiments, an individual treated with 2-((3-(4-cyanonaphthalen-1-yl) pyridin-4-yl thio)-2-methylpropanoic acid (1) displays aberrant uric acid levels, and (2) displays at least three of (a) elevated waist circumference: Men ≥40 inches (men) and ≥35 inches (women); (b) elevated triglycerides: ≥150 mg/dL; (c) reduced HDL: <40 mg/dL (men) and <50 mg/dL (women); (d) elevated blood pressure: ≥130/85 mm Hg or use of medication for hypertension; and (e) elevated fasting glucose: ≥100 mg/dL (5.6 mmol/L) or use of medication for hyperglycemia.

In some embodiments, an individual treated with 2-((3-(4-cyanonaphthalen-1-yl) pyridin-4-yl thio)-2-methylpropanoic acid (1) displays aberrant uric acid levels, and (2) suffers from kidney disease or kidney failure. In some embodiments, an individual treated with 2-((3-(4-cyanonaphthalen-1-yl) pyridin-4-yl thio)-2-methylpropanoic acid (1) displays aberrant uric acid levels, and (2) displays oliguria (decreased urine production. In some embodiments, an individual treated with 2-((3-(4-cyanonaphthalen-1-yl) pyridin-4-yl thio)-2-methylpropanoic acid (1) displays aberrant uric acid levels, and (2) produces less than 400 mL per day of urine (adults), produces less than 0.5 mL/kg/h of urine (children), or produces less than 1 mL/kg/h of urine (infants).

Uric Acid

In certain instances, purines (adenine, guanine), derived from food or tissue turnover (cellular nucleotides undergo continuous turnover), are catabolized in humans to their final oxidation product, uric acid. In certain instances, guanine is oxidized to xanthine, which is turn is further oxidized to uric acid by the action of xanthine oxidase; adenosine is converted to inosine which is further oxidized to hypoxanthine. In certain instances, xanthine oxidase oxidizes hypoxanthine to xanthine, and further to uric acid. In certain instances, as part of the reverse process, the enzyme hypoxanthine-guanine phosphoribosyltransferase (HGPRT) salvages guanine and hypoxanthine.

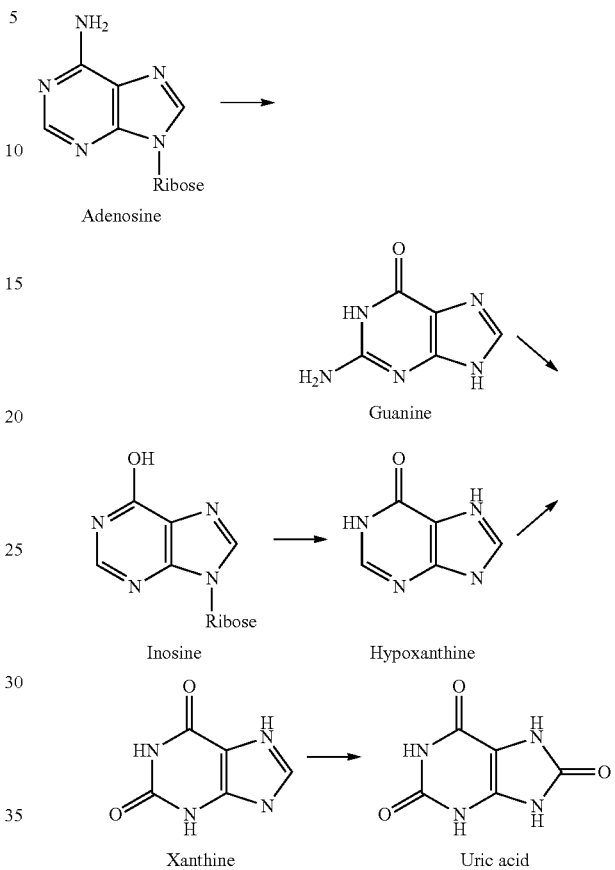

In certain instances, the keto form of uric acid is in equilibrium with the enol form which loses a proton at physiological pH to form urate. In certain instances, (e.g., under serum conditions (pH 7.40, 37° C.)), about 98% of uric acid is ionized as the monosodium urate salt. In certain instances, urate is a strong reducing agent and potent antioxidant. In humans, about half the antioxidant capacity of plasma comes from uric acid.

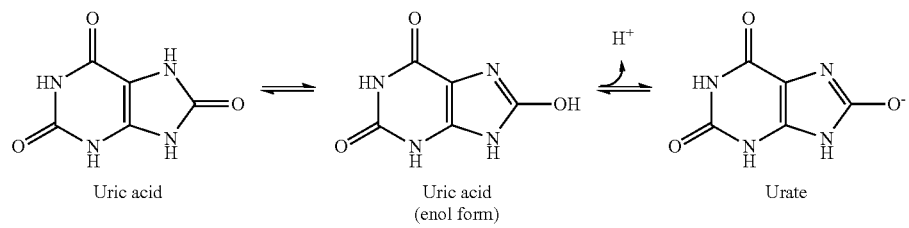

In certain instances, most uric acid dissolves in blood and passes to the kidneys, where it is excreted by glomerular filtration and tubular secretion. In certain instances, a substantial fraction of uric acid is reabsorbed by the renal tubules. One of the peculiar characteristics of the uric acid transport system is that, although the net activity of tubular function is reabsorption of uric acid, the molecule is both secreted and reabsorbed during its passage through the nephron. In certain instances, reabsorption dominates in the S1 and S3 segments of the proximal tubule and secretion dominates in the S2 segment. In certain instances, the bidirectional transport results in drugs that inhibit uric acid transport decreasing, rather than increasing, the excretion of uric acid, compromising their therapeutic usefulness. In certain instances, normal uric acid levels in human adults (5.1+/−0.93 mg/dL) are close to the limits of urate solubility (~7 mg/dL at 37° C.), which creates a delicate physiologic urate balance. In certain instances, the normal uric acid range for females is approximately 1 mg/dL below the male range.

Hyperuricemia

In certain instances, hyperuricemia is characterized by higher than normal blood levels of uric acid, sustained over long periods of time. In certain instances, increased blood urate levels may be due to enhanced uric acid production (~10-20%) and/or reduced renal excretion (~80-90%) of uric acid. In certain instances, causes of hyperuricemia may include:

Obesity/weight gain

Excessive alcohol use

Excessive dietary purine intake (foods such as shellfish, fish roe, scallops, peas lentils, beans and red meat, particularly offal—brains, kidneys, tripe, liver)

Certain medications, including low-dose aspirin, diuretics, niacin, cyclosporine, pyrazinamide, ethambutol, some high blood pressure drugs and some cancer chemotherapeutics, immunosuppressive and cytotoxic agents Specific disease states, particularly those associated with a high cell turnover rate (such as malignancy, leukemia, lymphoma or psoriasis), and also including high blood pressure, hemoglobin disorders, hemolytic anemia, sickle cell anemia, various nephropathies, myeloproliferative and lymphoproliferative disorders, hyperparathyroidism, renal disease, conditions associated with insulin resistance and diabetes mellitus, and in transplant recipients, and possibly heart disease Inherited enzyme defects Abnormal kidney function (e.g. increased ATP turn over, reduced glomerular urate filtration)

Exposure to lead (plumbism or "saturnine gout")

In certain instances, hyperuricemia may be asymptomatic, though is associated with the following conditions:

Gout

Gouty arthritis

Uric acid stones in the urinary tract (urolithiasis)

Deposits of uric acid in the soft tissue (tophi)

Deposits of uric acid in the kidneys (uric acid nephropathy)

Impaired kidney function, possibly leading to chronic and acute renal failure

Gout

Prevalence

The incidence of gout has increased over the past two decades and, in the United States, affects as much as 2.7% of the population aged 20 years and older, totaling over 5.1 million American adults. Gout is more common in men than women, (3.8% or 3.4 million men vs. 1.6% or 1.7 million women), typically affecting men in their 40's and 50's (although gout attacks can occur after puberty which sees an increase in uric acid levels). An increase in prevalence of gout from 2.9 to 5.2 per 1000 in the time period 1990 to 1999 was observed, with most of the increase occurring in those over the age of 65. Gout attacks are more common in women after menopause. In certain instances, gout is one of the most common forms of arthritis, accounting for approximately 5% of all arthritis cases. In certain instances, kidney failure and urolithiasis occur in 10-18% of individuals with gout and are common sources of morbidity and mortality from the disease.

Leading Causes

In most cases, gout is associated with hyperuricemia. In certain instances, individuals suffering from gout excrete approximately 40% less uric acid than nongouty individuals for any given plasma urate concentrations. In certain instances, urate levels increase until the saturation point is reached. In certain instances, precipitation of urate crystals occurs when the saturation point is reached. In certain instances, these hardened, crystallized deposits (tophi) form in the joints and skin, causing joint inflammation (arthritis). In certain instances, deposits are be made in the joint fluid (synovial fluid) and/or joint lining (synovial lining). Common areas for these deposits are the large toe, feet, ankles and hands (less common areas include the ears and eyes). In certain instances, the skin around an affected joint becomes red and shiny with the affected area being tender and painful to touch. In certain instances, gout attacks increase in frequency. In certain instances, untreated acute gout attacks lead to permanent joint damage and disability. In certain instances, tissue deposition of urate leads to: acute inflammatory arthritis, chronic arthritis, deposition of urate crystals in renal parenchyma and urolithiasis. In certain instances, the incidence of gouty arthritis increases 5 fold in individuals with serum urate levels of 7 to 8.9 mg/dL and up to 50 fold in individuals with levels >9 mg/dL (530 µmol/L). In certain instances, individuals with gout develop renal insufficiency and end stage renal disease (i.e., "gouty nephropathy"). In certain instances, gouty nephropathy is characterized by a chronic interstitial nephropathy, which is promoted by medullary deposition of monosodium urate.

In certain instances, gout includes painful attacks of acute, monarticular, inflammatory arthritis, deposition of urate crystals in joints, deposition of urate crystals in renal parenchyma, urolithiasis (formation of calculus in the urinary tract), and nephrolithiasis (formation of kidney stones). In certain instances, secondary gout occurs in individuals with cancer, particularly leukemia, and those with other blood disorders (e.g. polycythemia, myeloid metaplasia, etc).

Symptoms

In certain instances, attacks of gout develop very quickly, frequently the first attack occurring at night. In certain instances, symptoms include sudden, severe joint pain and extreme tenderness in the joint area, joint swelling and shiny red or purple skin around the joint. In certain instances, the attacks are infrequent lasting 5-10 days, with no symptoms between episodes. In certain instances, attacks become more frequent and may last longer, especially if the disorder is not controlled. In certain instances, episodes damage the affected joint(s) resulting in stiffness, swelling, limited motion and/or persistent mild to moderate pain.

Treatment

In certain instances, gout is treated by lowering the production of uric acid. In certain instances, gout is treated by increasing the excretion of uric acid. In certain instances, gout is treated by URAT 1, xanthine oxidase, xanthine dehydrogenase, xanthine oxidoreductase, a purine nucleoside phosphorylase (PNP) inhibitor, a uric acid transporter (URAT) inhibitor, a glucose transporter (GLUT) inhibitor, a GLUT-9 inhibitor, a solute carrier family 2 (facilitated glucose transporter), member 9 (SLC2A9) inhibitor, an organic anion transporter (OAT) inhibitor, an OAT-4 inhibitor, or combinations thereof. In general, the goals of gout treatment are to i) reduce the pain, swelling and duration of an acute attack, and ii) prevent future attacks and joint damage. In certain instances, gout attacks are treated successfully using a combination of treatments. In certain instances, gout is one of the most treatable forms of arthritis.

i) Treating the Gout Attack.

In certain instances, the pain and swelling associated with an acute attack of gout can be addressed with medications such as acetaminophen, steroids, nonsteroidal anti-inflammatory drugs (NSAIDs), adrenocorticotropic hormone (ACTH) or colchicine. In certain instances, proper medication controls gout within 12 to 24 hours and treatment is stopped after a few days. In certain instances, medication is used in conjunction with rest, increased fluid intake, ice-packs, elevation and/or protection of the affected area/s. In certain instances, the aforementioned treatments do not prevent recurrent attacks and they do not affect the underlying disorders of abnormal uric acid metabolism.

ii) Preventing Future Attacks.

In certain instances, reducing serum uric acid levels below the saturation level is the goal for preventing further gout attacks. In some cases, this is achieved by decreasing uric acid production (e.g. allopurinol), or increasing uric acid excretion with uricosuric agents (e.g. probenecid, sulfinpyrazone, benzbromarone).

In certain instances, allopurinol inhibits uric acid formation, resulting in a reduction in both the serum and urinary uric acid levels and becomes fully effective after 2 to 3 months.

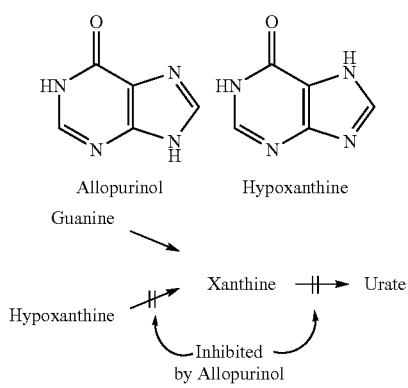

In certain instances, allopurinol is a structural analogue of hypoxanthine, (differing only in the transposition of the carbon and nitrogen atoms at positions 7 and 8), which inhibits the action of xanthine oxidase, the enzyme responsible for the conversion of hypoxanthine to xanthine, and xanthine to uric acid. In certain instances, it is metabolized to the corresponding xanthine analogue, alloxanthine (oxypurinol), which is also an inhibitor of xanthine oxidase. In certain instances, alloxanthine, though more potent in inhibiting xanthine oxidase, is less pharmaceutically acceptable due to low oral bioavailability. In certain instances, fatal reactions due to hypersensitivity, bone marrow suppression, hepatitis, and vasculitis have been reported with Allopurinol. In certain instances, the incidence of side effects may total 20% of all individuals treated with the drug. Treatment for disorders of uric acid metabolism has not evolved significantly in the following two decades since the introduction of allopurinol.

In certain instances, Uricosuric agents (e.g., probenecid, sulfinpyrazone, and benzbromarone) increase uric acid excretion. In certain instances, probenecid causes an increase in uric acid secretion by the renal tubules and, when used chronically, mobilizes body stores of urate. In certain instances, 25-50% of individuals treated with probenecid fail to achieve reduction of serum uric acid levels <6 mg/dL. In certain instances, insensitivity to probenecid results from drug intolerance, concomitant salicylate ingestion, and renal impairment. In certain instances, one-third of the individuals develop intolerance to probenecid. In certain instances, administration of uricosuric agents also results in urinary calculus, gastrointestinal obstruction, jaundice and anemia.

Plumbism or "Saturnine Gout"

In certain instances, excessive exposure to lead (lead poisoning or plumbism) results in "saturnine gout," a lead-induced hyperuricemia due to lead inhibition of tubular urate transport causing decreased renal excretion of uric acid. In certain instances, more than 50% of individuals suffering from lead nephropathy suffer from gout. In certain instances, acute attacks of saturnine gout occur in the knee more frequently than the big toe. In certain instances, renal disease is more frequent and more severe in saturnine gout than in primary gout. In certain instances, treatment consists of excluding the individual from further exposure to lead, the use of chelating agents to remove lead, and control of acute gouty arthritis and hyperuricaemia. In certain instances, saturnine gout is characterized by less frequent attacks than primary gout. In certain instances, lead-associated gout occurs in pre-menopausal women, an uncommon occurrence in non lead-associated gout.

Lesch-Nyhan Syndrome

In certain instances, Lesch-Nyhan syndrome (LNS or Nyhan's syndrome) affects about one in 100,000 live births. In certain instances, LNS is caused by a genetic deficiency of the enzyme hypoxanthine-guanine phosphoribosyltransferase (HGPRT). In certain instances, LNS is an X-linked recessive disease. In certain instances, LNS is present at birth in baby boys. In certain instances, the disorder leads to severe gout, poor muscle control, and moderate mental retardation, which appear in the first year of life. In certain instances, the disorder also results in self-mutilating behaviors (e.g., lip and finger biting, head banging) beginning in the second year of life. In certain instances, the disorder also results in gout-like swelling in the joints and severe kidney problems. In certain instances, the disorder leads neurological symptoms include facial grimacing, involuntary writhing, and repetitive movements of the arms and legs similar to those seen in Huntington's disease. The prognosis for individuals with LNS is poor. In certain instances, the life expectancy of an untreated individual with LNS is less than about 5 years. In certain instances, the life expectancy of a treated individual with LNS is greater than about 40 years of age.

Hyperuricemia and Other Diseases

In certain instances, hyperuricemia is found in individuals with cardiovascular disease (CVD) and/or renal disease. In certain instances, hyperuricemia is found in individuals with prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congenative heart failure, stroke, tumor lysis syndrome, endothelial dysfunction, oxidative stress, elevated renin levels, elevated endothelin levels, and/or elevated C-reactive protein levels. In certain instances, hyperuricemia is found in individuals with obesity (e.g., central obesity), high blood pressure, hyperlipidemia, and/or impaired fasting glucose. In certain instances, hyperuricemia is found in individuals with metabolic syndrome. In certain instances, gouty arthritis is indicative of an increased risk of acute myocardial infarction. In some embodiments, administration of 2-((3-(4-cyanonaphthalen-1-yl)pyridin-4-yl)thio)-2-methylpropanoic acid to an individual are useful for decreasing the likelihood of a clinical event associated with a disease or condition linked to hyperuricemia, including, but not limited to, prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congenative heart failure, stroke, tumor lysis syndrome, endothelial dysfunction, oxidative stress, elevated renin levels, elevated endothelin levels, and/or elevated C-reactive protein levels.

One embodiment provides a method of treating or preventing a condition characterized by abnormal tissue or organ levels of uric acid in an individual comprising administering to the individual an effective amount of 2-((3-(4-cyanonaphthalen-1-yl) pyridin-4-yl thio)-2-methylpropanoic acid. Another embodiment provides the method wherein the condition is gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis, sarcoidosis, hypoxanthine-guanine phosphoribosyltransferase (HPRT) deficiency or a combination thereof. Another embodiment provides the method wherein the condition is gout.

Another embodiment provides the method further comprising administering a second agent effective for the treatment of the gout. Another embodiment provides the method wherein the second agent is a URAT 1 inhibitor, a xanthine oxidase inhibitor, a xanthine dehydrogenase, a xanthine oxidoreductase inhibitor, or combinations thereof. Another embodiment provides the method wherein the second agent is 2-((5-bromo-4-(4-cyclopropyl-1-naphthalenyl)-4H-1,2,4-triazol-3-yl)thio)acetic acid, allopurinol, febuxostat, FYX-051, or combinations thereof.

In some embodiments, 2-((3-(4-cyanonaphthalen-1-yl) pyridin-4-yl)thio)-2-methylpropanoic acid is administered to an individual suffering from a disease or condition requiring treatment with a diuretic. In some embodiments, 2-((3-(4-cyanonaphthalen-1-yl)pyridin-4-yl)thio)-2-methylpropanoic acid is administered to an individual suffering from a disease or condition requiring treatment with a diuretic, wherein the diuretic causes renal retention of urate. In some embodiments, the disease or condition is congestive heart failure or essential hypertension.

In some embodiments, administration of 2-((3-(4-cyanonaphthalen-1-yl)pyridin-4-yl)thio)-2-methylpropanoic acid to an individual is useful for improving motility or improving quality of life.

In some embodiments, administration of 2-((3-(4-cyanonaphthalen-1-yl)pyridin-4-yl)thio)-2-methylpropanoic acid to an individual is useful for treating or decreasing the side effects of cancer treatment.

In some embodiments, administration of 2-((3-(4-cyanonaphthalen-1-yl)pyridin-4-yl)thio)-2-methylpropanoic acid to an individual is useful for decreasing kidney toxicity of cis-platin.

Methods of Reducing Serum Uric Acid Levels

Provided herein, in some embodiments, are methods for reducing serum uric acid levels by administration of 2-((3-(4-cyanonaphthalen-1-yl) pyridin-4-yl thio)-2-methylpropanoic acid. In some embodiments, a method of reducing serum uric acid levels in a mammal comprises administering 2-((3-(4-cyanonaphthalen-1-yl) pyridin-4-yl thio)-2-methylpropanoic acid. In certain embodiments, the mammal is a human. In some embodiments, a method of reducing serum uric acid levels in a human comprises administering to the human 2-((3-(4-cyanonaphthalen-1-yl) pyridin-4-yl thio)-2-methylpropanoic acid, or a pharmaceutically acceptable salt or ester thereof.

In some embodiments, a method for reducing serum uric acid levels comprises administering less than 100 mg of 2-((3-(4-cyanonaphthalen-1-yl) pyridin-4-yl thio)-2-methylpropanoic acid. In certain embodiments, the method comprises administering less than 50 mg of 2-((3-(4-cyanonaphthalen-1-yl) pyridin-4-yl thio)-2-methylpropanoic acid. In some embodiments, the method of reducing serum uric acid levels comprises administering less than 150 mg, less than 125 mg, less than 100 mg, less than 90 mg, less than 80 mg, less than 70 mg, less than 60 mg, less than 50 mg, less than 45 mg, less than 40 mg, less than 35 mg, less than 30 mg, less than 25 mg, less than 20 mg, less than 10 mg, or less than 5 mg of 2-((3-(4-cyanonaphthalen-1-yl) pyridin-4-yl thio)-2-methylpropanoic acid. In some embodiments, the method for reducing serum uric acid levels comprises administering less than 2 mg or less than 1 mg of 2-((3-(4-cyanonaphthalen-1-yl) pyridin-4-yl thio)-2-methylpropanoic acid. In some embodiments, the method of reducing serum uric acid levels comprises administering not more than 150 mg, not more than 125 mg, not more than 100 mg, not more than 90 mg, not more than 80 mg, not more than 70 mg, not more than 60 mg, not more than 50 mg, not more than 45 mg, not more than 40 mg, not more than 35 mg, not more than 30 mg, not more than 25 mg, not more than 20 mg, not more than 10 mg, or not more than 5 mg of 2-((3-(4-cyanonaphthalen-1-yl) pyridin-4-yl thio)-2-methylpropanoic acid. In some embodiments, the method for reducing serum uric acid levels comprises administering not more than 2 mg or not more than 1 mg of 2-((3-(4-cyanonaphthalen-1-yl) pyridin-4-yl thio)-2-methylpropanoic acid.

In certain embodiments, a method for reducing serum uric acid levels comprises administering about 40 mg of 2-((3-(4-cyanonaphthalen-1-yl) pyridin-4-yl thio)-2-methylpropanoic acid. In some embodiments, the method comprises administering about 20 mg of 2-((3-(4-cyanonaphthalen-1-yl) pyridin-4-yl thio)-2-methylpropanoic acid. In other embodiments, the method comprises administering about 5 mg of 2-((3-(4-cyanonaphthalen-1-yl) pyridin-4-yl thio)-2-methylpropanoic acid. In certain embodiments, the method of reducing serum uric acid levels comprises administering about 150 mg, about 125 mg, about 100 mg, about 90 mg, about 80 mg, about 70 mg, about 60 mg, about 50 mg, about 45 mg, about 40 mg, about 35 mg, about 30 mg, about 25 mg, about 20 mg, about 10 mg, or about 5 mg of 2-((3-(4-cyanonaphthalen-1-yl) pyridin-4-yl thio)-2-methylpropanoic acid. In some embodiments, the method for reducing serum uric acid levels comprises administering about 4 mg, about 3 mg, about 2 mg, about 1 mg or about 0.5 mg of 2-((3-(4-cyanonaphthalen-1-yl) pyridin-4-yl thio)-2-methylpropanoic acid.

In some embodiments, a method for reducing serum uric acid levels comprises administering less than 100 mg per day of 2-((3-(4-cyanonaphthalen-1-yl) pyridin-4-yl thio)-2-methylpropanoic acid. In certain embodiments, the method comprises administering less than 50 mg per day of 2-((3-(4-cyanonaphthalen-1-yl) pyridin-4-yl thio)-2-methylpropanoic acid. In some embodiments, the method of reducing serum uric acid levels comprises administering less than 150 mg per day, less than 125 mg per day, less than 100 mg per day, less than 90 mg per day, less than 80 mg per day, less than 70 mg per day, less than 60 mg per day, less than 50 mg per day, less than 45 mg per day, less than 40 mg per day, less than 35 mg per day, less than 30 mg per day, less than 25 mg per day, less than 20 mg per day, less than 10 mg per day, or less than 5 mg per day of 2-((3-(4-cyanonaphthalen-1-yl) pyridin-4-yl thio)-2-methylpropanoic acid. In some embodiments, the method for reducing serum uric acid levels comprises administering less than 2 mg per day or less than 1 mg per day of 2-((3-(4-cyanonaphthalen-1-yl) pyridin-4-yl thio)-2-methylpropanoic acid. In some embodiments, the method of reducing serum uric acid levels comprises administering not more than 150 mg per day, not more than 125 mg per day, not more than 100 mg per day, not more than 90 mg per day, not more than 80 mg per day, not more than 70 mg per day, not more than 60 mg per day, not more than 50 mg per day, not more than 45 mg per day, not more than 40 mg per day, not more than 35 mg per day, not more than 30 mg per day, not more than 25 mg per day, not more than 20 mg per day, not more than 10 mg per day, or not more than 5 mg per day of 2-((3-(4-cyanonaphthalen-1-yl) pyridin-4-yl thio)-2-methylpropanoic acid. In some embodiments, the method for reducing serum uric acid levels comprises administering not more than 2 mg per day or not more than 1 mg per day of 2-((3-(4-cyanonaphthalen-1-yl) pyridin-4-yl thio)-2-methylpropanoic acid.

In certain embodiments, a method for reducing serum uric acid levels comprises administering about 40 mg per day of 2-((3-(4-cyanonaphthalen-1-yl) pyridin-4-yl thio)-2-methylpropanoic acid. In some embodiments, the method comprises administering about 20 mg per day of 2-((3-(4-cyanonaphthalen-1-yl) pyridin-4-yl thio)-2-methylpropanoic acid. In other embodiments, the method comprises administering about 5 mg per day of 2-((3-(4-cyanonaphthalen-1-yl) pyridin-4-yl thio)-2-methylpropanoic acid. In certain embodiments, the method of reducing serum uric acid levels comprises administering about 150 mg per day, about 125 mg per day, about 100 mg per day, about 90 mg per day, about 80 mg per day, about 70 mg per day, about 60 mg per day, about 50 mg per day, about 45 mg per day, about 40 mg per day, about 35 mg per day, about 30 mg per day, about 25 mg per day, about 20 mg per day, about 10 mg per day, or about 5 mg per day of 2-((3-(4-cyanonaphthalen-1-yl) pyridin-4-yl thio)-2-methylpropanoic acid. In some embodiments, the method for reducing serum uric acid levels comprises administering about 4 mg per day, about 3 mg per day, about 2 mg per day, about 1 mg per day or about 0.5 mg per day of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 0.3 mg/dL 24 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 0.5 mg/dL 24 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 0.8 mg/dL 24 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 1 mg/dL 24 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 2 mg/dL 24 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 3 mg/dL 24 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 4 mg/dL 24 hours after administration of 2-((3-(4-cyanonaphthalen-1-yl) pyridin-4-yl thio)-2-methylpropanoic acid.

In certain embodiments of a method for reducing serum uric acid levels, the serum uric acid levels are reduced by at least 0.5 mg/dL 48 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 0.8 mg/dL 48 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 1 mg/dL 48 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 2 mg/dL 48 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 3 mg/dL 48 hours after administration of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 0.5 mg/dL 72 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 0.8 mg/dL 72 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 1 mg/dL 72 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 2 mg/dL 72 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 3 mg/dL 72 hours after administration of 2-((3-(4-cyanonaphthalen-1-yl) pyridin-4-yl thio)-2-methylpropanoic acid.

In certain embodiments of a method for reducing serum uric acid levels, the serum uric acid levels are reduced by at least 0.5 mg/dL at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 0.8 mg/dL at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 1 mg/dL at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 2 mg/dL at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 3 mg/dL at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 4 mg/dL at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid.

In some embodiments of a method for reducing serum uric acid levels, the serum uric acid levels are reduced by about 0.5 mg/dL 24 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 0.8 mg/dL 24 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 1 mg/dL 24 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 2 mg/dL 24 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 3 mg/dL 24 hours after administration of 2-((3-(4-cyanonaphthalen-1-yl) pyridin-4-yl thio)-2-methylpropanoic acid.

In certain embodiments of a method for reducing serum uric acid levels, the serum uric acid levels are reduced by about 0.5 mg/dL 48 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 0.8 mg/dL 48 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 1 mg/dL 48 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 2 mg/dL 48 hours after administration of 2-((3-(4-cyanonaphthalen-1-yl) pyridin-4-yl thio)-2-methylpropanoic acid. In certain embodiments of a method for reducing serum uric acid levels are reduced by about 3 mg/dL 48 hours after administration of 2-((3-(4-cyanonaphthalen-1-yl) pyridin-4-yl thio)-2-methylpropanoic acid.

In some embodiments of a method for reducing serum uric acid levels, the serum uric acid levels are reduced by about 0.5 mg/dL 72 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 0.8 mg/dL 72 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 1 mg/dL 72 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 2 mg/dL 72 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 3 mg/dL 72 hours after administration of 2-((3-(4-cyanonaphthalen-1-yl) pyridin-4-yl thio)-2-methylpropanoic acid.

In certain embodiments of a method for reducing serum uric acid levels, the serum uric acid levels are reduced by about 0.5 mg/dL at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 0.8 mg/dL at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 1 mg/dL at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 2 mg/dL at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 3 mg/dL at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 4 mg/dL at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid.

In certain embodiments of a method for reducing serum uric acid levels, the serum uric acid levels are reduced by at least 10% from baseline 24 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 15% from baseline 24 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 20% from baseline 24 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 30% from baseline 24 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 40% from baseline 24 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 50% from baseline 24 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 60% from baseline 24 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 10%, at least 20%, at least 30%, at least 40%, at least 50%, or at least 60% from baseline 24 hours after administration of 2-((3-(4-cyanonaphthalen-1-yl) pyridin-4-yl thio)-2-methylpropanoic acid.

In certain embodiments of a method for reducing serum uric acid levels, the serum uric acid levels are reduced by about 10% from baseline 48 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 20% from baseline 48 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 30% from baseline 48 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 40% from baseline 48 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 50% from baseline 48 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 10%, at least 20%, at least 30%, at least 40%, at least 50%, or at least 60% from baseline 48 hours after administration of 2-((3-(4-cyanonaphthalen-1-yl) pyridin-4-yl thio)-2-methylpropanoic acid.

In certain embodiments of a method for reducing serum uric acid levels, the serum uric acid levels are reduced by at least 15% from baseline 72 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 20% from baseline 72 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 30% from baseline 72 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 40% from baseline 72 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 10%, at least 15%, at least 20%, at least 25%, at least 30%, at least 35%, at least 40%, at least 50%, or at least 60% from baseline 72 hours after administration of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 10% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 15% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 20% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 30% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by at least 40% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 50% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 60% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid.

In certain embodiments of a method for reducing serum uric acid levels, the serum uric acid levels are reduced by about 15% from administration of 24 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 20% from baseline 24 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 30% from baseline 24 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 40% from baseline 24 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 50% from baseline 24 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 60% from baseline 24 hours after administration of 2-((3-(4-cyanonaphthalen-1-yl) pyridin-4-yl thio)-2-methylpropanoic acid.

In some embodiments of a method for reducing serum uric acid levels, the serum uric acid levels are reduced by about 10% from baseline 48 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 15% from baseline 48 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 20% from baseline 48 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 30% from baseline 48 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 40% from baseline 48 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 50% from baseline 48 hours after administration of 2-((3-(4-cyanonaphthalen-1-yl) pyridin-4-yl thio)-2-methylpropanoic acid. In some embodiments of a method for reducing serum uric acid levels are reduced by about 60% from baseline 48 hours after administration of 2-((3-(4-cyanonaphthalen-1-yl) pyridin-4-yl thio)-2-methylpropanoic acid.

In some embodiments of a method for reducing serum uric acid levels, the serum uric acid levels are reduced by about 10% from baseline 72 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 15% from baseline 72 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 20% from baseline 72 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 30% from baseline 72 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 40% from baseline 72 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 50% from baseline 72 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 60% from baseline 72 hours after administration of 2-((3-(4-cyanonaphthalen-1-yl) pyridin-4-yl thio)-2-methylpropanoic acid.

In certain embodiments of a method for reducing serum uric acid levels, the serum uric acid levels are reduced by about 10% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 15% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 20% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 30% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 40% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In some embodiments of a method for reducing serum uric acid levels, the serum uric acid levels are reduced by about 50% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 60% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid. In certain embodiments of a method for reducing serum uric acid levels, the serum uric acid levels are reduced by about 70% from baseline at 6 hours, 12 hours, 18 hours, 24 hours, 30 hours, 36 hours, 42 hours, 48 hours, 54 hours, 60 hours, 72 hours, 84 hours, 96 hours, 108 hours, or 120 hours after administration of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 0.5 mg/dL 24 hours after administration of about 1 mg of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 0.5 mg/dL 48 hours after administration of about 1 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 0.5 mg/dL 72 hours after administration of about 1 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 1 mg/dL 24 hours after administration of about 1 mg of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 1 mg/dL 48 hours after administration of about 1 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 1 mg/dL 72 hours after administration of about 1 mg of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 0.5 mg/dL 24 hours after administration of about 2 mg of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 0.5 mg/dL 48 hours after administration of about 2 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 0.5 mg/dL 72 hours after administration of about 2 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 1 mg/dL 24 hours after administration of about 2 mg of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 1 mg/dL 48 hours after administration of about 2 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 1 mg/dL 72 hours after administration of about 2 mg of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 1 mg/dL 24 hours after administration of about 5 mg of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 1 mg/dL 48 hours after administration of about 5 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 1 mg/dL 72 hours after administration of about 5 mg of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 1 mg/dL 24 hours after administration of about 20 mg of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 1 mg/dL 48 hours after administration of about 20 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 1 mg/dL 72 hours after administration of about 20 mg of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 2 mg/dL 24 hours after administration of about 40 mg of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 2 mg/dL 48 hours after administration of about 40 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 1 mg/dL 72 hours after administration of about 40 mg of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 5% from baseline 24 hours after administration of about 1 mg of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 10% from baseline 48 hours after administration of about 1 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 15% from baseline 48 hours after administration of about 1 mg of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 8% from baseline 24 hours after administration of about 2 mg of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 10% from baseline 24 hours after administration of about 2 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 15% from baseline 24 hours after administration of about 2 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 10% from baseline 48 hours after administration of about 2 mg of 2-((3-(4-cyanonaphthalen-1-yl) pyridin-4-yl thio)-2-methylpropanoic acid. In certain embodiments of a method for reducing serum uric acid levels are reduced by at least 15% from baseline 48 hours after administration of about 2 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 15% from baseline 72 hours after administration of about 2 mg of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 20% from baseline 24 hours after administration of about 5 mg of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 20% from baseline 48 hours after administration of about 5 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 10% from baseline 72 hours after administration of about 5 mg of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 40% from baseline 24 hours after administration of about 20 mg of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 30% from baseline 48 hours after administration of about 20 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 20% from baseline 72 hours after administration of about 20 mg of 2-((3-(4-cyanonaphthalen-1-yl) pyridin-4-yl thio)-2-methylpropanoic acid.

In some embodiments of a method for reducing serum uric acid levels, the serum uric acid levels are reduced by at least 50% from baseline after administration of about 40 mg of 2-((3-(4-cyanonaphthalen-1-yl) pyridin-4-yl thio)-2-methylpropanoic acid. In certain embodiments of a method for reducing serum uric acid levels, the serum uric acid levels are reduced by at least 40% from baseline 48 hours after administration of about 40 mg of 2-((3-(4-cyanonaphthalen-1-yl) pyridin-4-yl thio)-2-methylpropanoic acid. In some embodiments of a method for reducing serum uric acid levels, the serum uric acid levels are reduced by at least 20% from baseline 72 hours after administration of about 40 mg of 2-((3-(4-cyanonaphthalen-1-yl) pyridin-4-yl thio)-2-methylpropanoic acid.

Kits

The compounds, compositions and methods described herein provide kits for the treatment of disorders, such as the ones described herein. These kits comprise a compound, compounds or compositions described herein in a container and, optionally, instructions teaching the use of the kit according to the various methods and approaches described herein. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

2-((3-(4-cyanonaphthalen-1-yl)pyridin-4-yl)thio)-2-methylpropanoic acid can be utilized for diagnostics and as research reagents. For example, 2-((3-(4-cyanonaphthalen-1-yl)pyridin-4-yl)thio)-2-methylpropanoic acid, either alone or in combination with other compounds, can be used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Besides being useful for human treatment, 2-((3-(4-cyanonaphthalen-1-yl)pyridin-4-yl)thio)-2-methylpropanoic acid and formulations thereof, may be useful for veterinary treatment of companion animals, exotic animals and farm animals, including mammals, rodents, and the like. More preferred animals include horses, dogs, and cats.

EXAMPLES

The examples and preparations provided below further illustrate and exemplify the present invention. The scope of the present invention is not limited in any way by the scope of the following examples.

Example 1: Preparation of 2-((3-(4-cyanonaphthalen-1-yl)pyridin-4-yl)thio)-2-methylpropanoic acid 2-((3-(4-cyanonaphthalen-1-yl)pyridin-4-yl)thio)-2-methylpropanoic acid was prepared as described in U.S. provisional patent application 61/355,491 and PCT/US11/40585 and as described below.

Step A

A mixture of 3-bromo-4-chloropyridine (10.0 g, 52 mmol) and sodium sulfide (12.2 g, 156 mmol) in DMF (100 mL) was stirred at 130° C. for 2 hours. The mixture was cooled in an ice water bath, and aqueous HCl (6N, 45 mL) added dropwise with rigorous stirring. The resulting yellow paste was concentrated using rotary evaporation on a water bath (80° C.) to dryness. The resulting yellow solid was extracted with methanol (4×50 mL), and the combined extracts concentrated to give a yellow solid (9.5 g, 96%).

Step B

A mixture of 3-bromopyridine-4-thiol (step A, 4.75 g, 25 mmol), ethyl 2-bromoisobutyrate (9.75 g, 50 mmol), and sodium carbonate (7.95 g, 75 mmol) in DMF (50 mL) was stirred at 60° C. for 1 hour. The reaction mixture was partitioned between water (100 mL) and ethyl acetate (100 mL). The organic layer was washed with water (2×100 mL) and saturated sodium chloride (100 mL). The aqueous washes were back extracted with ethyl acetate (2×100 mL). The combined organic layers were dried over sodium sulfate, concentrated, and purified by normal phase chromatography (0-25% ethyl acetate in hexane gradient) to yield ethyl 2-(3-bromopyridin-4-ylthio)-2-methylpropanoate as a pale yellow oil (6.6 g, 88%).

Step C

To a mixture of (4-cyanonaphthalen-1-yl) boronic acid and Pd(dppf)Cl$_2$ were added a solution of ethyl 2-((3-bromopyridin-4-ylthio)-2-methylpropanoate in THF, acetonitrile, and sodium carbonate. The resulting mixture was degassed by nitrogen bubbling for 1 minute, and heated to 150° C. for 30 minutes under microwave irradiation. The mixture was loaded on to a ISCO loading cartridge and eluded with a gradient of 0-100% ethyl acetate in hexane on a ISCO column to yield ethyl 2-((3-(4-cyanonaphthalen-1-yl)pyridin-4-yl)thio)-2-methylpropanoate.

Step D

Methanol and sodium hydroxide were added to ethyl 2-((3-(4-cyanonaphthalen-1-yl)pyridin-4-yl)thio)-2-methylpropanoate and stirred at ambient temperature for 2 hours. The volume was reduced by rotary evaporation. To the residue was added HCl (6 N aqueous) with stirring until pH 6, resulting in the formation of a white precipitate, which was isolated by filtration. The solid was washed with water, air dried and dried under vacuum (P$_2$O$_5$) overnight to yield 2-((3-(4-cyanonaphthalen-1-yl)pyridin-4-yl)thio)-2-methylpropanoic acid.

$^1$H NMR (400 MHz, DMSO-d$_6$) δ ppm 13.22 (bs, 1H), 8.61 (s, 1H), 8.34-8.39 (m, 2H), 8.02 (dd, J=7.2, 7.2 Hz, 1H), 7.74-7.79 (m, 2H), 7.60 (dd, J=7.6, 7.6 Hz, 1H), 7.44-7.53 (m, 2H), 1.61 (s, 3H), 1.54 (s, 3H).

MS (m/z), M+1, 349.14

Example 2: Evaluation with URAT1-Model Assay

HEK293 human embryonic kidney cells (ATCC# CRL-1573) were propagated in EMEM tissue culture medium as described by ATCC in an atmosphere of 5% CO$_2$ and 95% air. Transfections of HEK293 cells with a model URAT1 construct was performed using L2000 transfection reagent (Invitrogen) as described by the manufacturer. After 24 h the transfected cells were split into 10 cm tissue culture plates and grown for 1 day after which the medium was replaced with fresh growth medium containing G418 (Gibco) at 0.5 mg/ml final concentration. Drug-resistant colonies were selected after approximately 8 days and then tested for $^{14}$C-uric acid transport activity. The HEK293/URAT1-model cells are plated on Poly-D-Lysine Coated 96-well Plates at a density of 125,000 cells per well.

Cells were grown overnight (20-26 hours) at 37° C. in an incubator. Plates were allowed to come to room temperature and media was washed out with one wash of 250 µl of Wash Buffer (125 mM Na Gluconate, 10 mM Hepes ph 7.3). 2-((3-(4-cyanonaphthalen-1-yl)pyridin-4-yl)thio)-2-methylpropanoic acid or vehicle is added in assay buffer with $^{14}$C-uric acid for a final concentration of 125 µM Uric Acid with a specific activity of 54 mCi/mmol. Assay Buffer is 125 mM Sodium Gluconate, 4.8 mM Potassium Gluconate, 1.2 mM Potassium phosphate, monobasic, 1.2 mM magnesium sulfate, 1.3 mM Ca Gluconate, 5.6 mM Glucose, 25 mM HEPES, pH 7.3. Plates were incubated at room temperature for 10 minutes then washed 3 times with 50 µl Wash Buffer and 3 times with 250 µl Wash Buffer. Microscint 20 Scintillation Fluid was added and plates were incubated overnight at room temperature to equilibrate. Plates are then read on the TopCount Plate Reader and an EC50 value generated. (See Enomoto et al, Nature, 2002, 417, 447-451 and Anzai et al, J. Biol. Chem., 2004, 279, 45942-45950.)

2-((3-(4-cyanonaphthalen-1-yl)pyridin-4-yl)thio)-2-methylpropanoic acid was tested according to the protocol described above against URAT-1 model. 2-((3-(4-cyanonaphthalen-1-yl)pyridin-4-yl)thio)-2-methylpropanoic acid has an EC$_{50}$ value ≤0.05 µM.

Example 3: Single-Dose Phase I Clinical Trial 2-((3-(4-cyanonaphthalen-1-yl)pyridin-4-yl)thio)-2-methylpropanoic acid was investigated according to the clinical trial described below.

Study

A Phase 1, Randomized, Double-Blind, Placebo-Controlled Study to Evaluate Safety, Tolerability, Pharmacokinetics and Preliminary Food Effect of Single Doses of a URAT1 Inhibitor, in Healthy Adult Male Volunteers.

Objectives

To assess safety, tolerability, pharmacokinetics and uricosuric effects after oral administration as single doses of a tablet formulation and the effect of food on bioavailability.

Investigational Plan/Study Design

Subjects receive a single, oral dose of active or placebo, at the following doses:
Group 1: 2 mg (fasted);
Group 2: 5 mg (fasted);
Group 3: 5 mg (fed);
Group 4: 20 mg (fasted) [sentinel dosing];
Group 5: 20 mg (fed);
Group 6: 40 mg (fasted)

Study Details

Subjects 48 subjects in 6 dose groups, 8 subjects/group, are randomized 3:1 to receive active (6/group) or placebo (2/group). All study procedures are the same regardless of whether subject receives active or placebo. The total duration of subject participation, including screening period, is ~2-4 weeks, and the total volume of blood collected from each subject during the entire study <500 mL, (less than typically collected during a volunteer blood donation).

Study Medication 5 mg and 20 mg, active and placebo, tablets packaged in 35 count HDPE bottles, stored at controlled room temperature (15-30° C.). Placebo tablets are designed to match the active tablets—identical size, form, taste, and color, and containing the same excipients. 2 mg was dosed as an oral solution.

Participation Criteria

Inclusion Criteria:

Healthy male adults, age 18-45, with body weight >50 kg and BMI 18-30 kg/m$^2$.

All laboratory parameters (chemistry, hematology, urinalysis) within normal limits; sUA≥5 mg/dL.

Subjects free of clinically significant disease and have normal physical examination, including normal blood pressure (90-140/50-90 mmHg), heart rate (50-100 bpm), body temp (35.0-37.5° C.) and respiratory rate (8-20 bpm), and no electrocardiogram abnormalities.

Exclusion Criteria:

Any illness within 1 week of dosing, or HIV, Hep B or Hep C positive.

History of kidney stones, significant metabolic, hematological, pulmonary, cardiovascular, gastrointestinal, neurologic, hepatic, renal, urological, psychiatric disorders, cardiac abnormalities, or major surgery within past 3 months.

Donation of blood or plasma, or received an investigational therapy within previous 3 months.

Any drug treatment, including prescribed/OTC medicines or herbal preparations, in previous 14 days.

History of drug addiction, excessive alcohol use, heavy caffeine drinker, use of tobacco products within previous 30 days, and/or refusal to abstain from tobacco, alcohol, caffeine during the study.

Refusal to refrain from strenuous exercise during study.

Subjects with allergies, or hypersensitivity to any ingredient in the investigational products.

Summary of Study Activities/Schedule of Events

FIG. 1A shows a schematic representation of the schedule of events.

Screening Visit Days −21 to −3

After obtaining written informed consent, subjects are screened to confirm study eligibility.

Pretreatment: Day −2 to −1

Subjects are admitted to CRU ~48 hours prior to dosing and remain at the center until all study assessments complete, with standardized meals served at appropriate times.

The following is performed on Day −1 beginning 24 hours pre-dose:

Urine (total catch) collected over the following intervals: −24 to −18, −18 to −12, −12 to 0 hours;

Serum samples collected at −24, −18 and −12 hrs.

Treatment Period: Days 1 to 4

The following is performed during the treatment period:

Subjects dosed on the morning of Day 1 with ~240 mL of room temp water.

Fasted: subjects are dosed after overnight fast >10 hours and remain fasted until >4 hours post-dose.

Fed: subjects fast overnight for >10 hours, then are dosed 30 mins after completing standard moderate fat breakfast (no high fructose corn syrup).

Plasma samples are collected at:

−0.5 (pre dose);

0.25, 0.5, 0.75, 1, 1.5, 2, 2.5, 3, 4, 5, 6, 8, 10, 12, 24, 30, 36, 48, 54, 60, and 72 hours (post-dose)

Additional plasma sample (20 mL) at 4 hours post-dose (metabolite testing)

Urine samples (total catch) are collected over the following intervals:

0 to 6, 6 to 12, 12 to 24, 24 to 36, 36 to 48, 48 to 60, and 60 to 72 hours post-dose.

Serum samples are collected at:

0 hours (within 30 minutes dosing), 6, 12, 24, 30, 36, 48, 54, 60 and 72 hours post-dose.

PD samples are frozen (−20° C.) and stored; all samples from a given subject assayed in a single analytical run.

End of Study

Subjects remain at the study site until all scheduled samples are collected through the morning of Day 4. Upon completion of all study-related procedures and assessments, subjects discharged.

Subjects return to study site for follow-up visit on Day 8±1, for physical exam, vital signs, ECG, safety laboratory tests, AEs and concomitant medications.

Adverse Events, Serious Adverse Events and Removal from the Trial

An adverse event (AE) is any untoward medical occurrence associated with the use of a drug, whether or not considered drug related. Adverse events are continuously monitored throughout the study.

The severity of AEs should be identified as mild, moderate, severe or life threatening. The relationship of the AE to the study medication should be identified as Not Related, Unlikely, or Possible.

A serious adverse event (SAE) is any AE that results in: death, life-threatening AE, hospitalization, a persistent or significant disability/incapacity or substantial disruption of the ability to conduct normal life functions, or a congenital anomaly/birth defect.

A subject may be withdrawn for a protocol violation, a serious AE, a clinically significant change in a laboratory parameter or at the request of the subject. Subjects withdrawing after dosing not replaced.

Evaluation of Results

Pharmacokinetics (PK), Pharmacodynamics (PD) and Safety & Adverse Events are evaluated. All dosed subjects who have evaluable PK data make up the PK Population. All dosed subjects make up the Safety Population. All sampling times are in relation to the beginning of dosing (subject taking first tablet).

Example 4A: Single-Dose Clinical Trial Results for Group 1

2-((3-(4-cyanonaphthalen-1-yl)pyridin-4-yl)thio)-2-methylpropanoic acid was investigated according to the clinical trial described in Example 3.

Results for the eight subjects in Group 1 (2 mg, fasted) are shown below. Subjects 1 and 2 received placebo; subjects 3-8 received active.

Figure 2A:
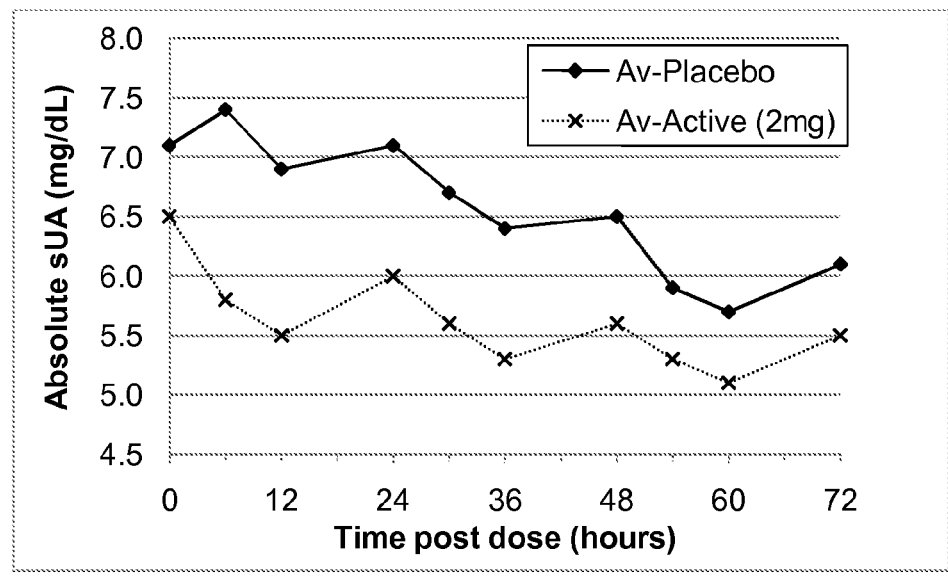
FIG. 2A shows the absolute serum uric acid concentrations (mg/dL) measured 0-72 hours post-dose for Group 1 (2 mg, fasted). Subjects 1 and 2 received placebo; subjects 3-8 received active.

Absolute sUA concentrations (mg/dL) from 0-72 hours post-dose are shown in the table below, and presented in graphical form in FIG. 2A.

| | Absolute sUA concentration (mg/dL) | | | | | | | | | |
|---|---|---|---|---|---|---|---|---|---|---|
| | Subject number | | | | | | | | Mean | Mean |
| Time | 1 | 2 | 3 | 4 | 5 | 6 | 7 | 8 | Placebo | (3-8) |
| 0 | 8.1 | 6.0 | 7.4 | 7.3 | 6.6 | 6.3 | 6.2 | 5.1 | 7.1 | 6.5 |
| 6 | 8.5 | 6.2 | 6.6 | 6.6 | 6.0 | 5.9 | 5.1 | 4.7 | 7.4 | 5.8 |
| 12 | 8.0 | 5.8 | 6.4 | 6.3 | 5.6 | 5.5 | 4.9 | 4.2 | 6.9 | 5.5 |
| 24 | 8.0 | 6.2 | 6.8 | 6.4 | 5.9 | 6.2 | 5.7 | 4.7 | 7.1 | 6.0 |
| 30 | 7.7 | 5.7 | 6.5 | 6.3 | 5.6 | 5.7 | 5.3 | 4.3 | 6.7 | 5.6 |
| 36 | 7.2 | 5.5 | 6.3 | 6.1 | 5.2 | 5.3 | 4.8 | 4.0 | 6.4 | 5.3 |
| 48 | 7.4 | 5.5 | 6.8 | 6.4 | 5.4 | 5.8 | 5.1 | 4.3 | 6.5 | 5.6 |
| 54 | 6.7 | 5.0 | 6.5 | 5.9 | 5.1 | 5.2 | 4.8 | 4.0 | 5.9 | 5.3 |
| 60 | 6.5 | 4.9 | 6.6 | 5.9 | 5.0 | 4.9 | 4.6 | 3.8 | 5.7 | 5.1 |
| 72 | 6.9 | 5.3 | 6.5 | 6.1 | 5.3 | 5.8 | 5.0 | 4.2 | 6.1 | 5.5 |

Figure 2B:
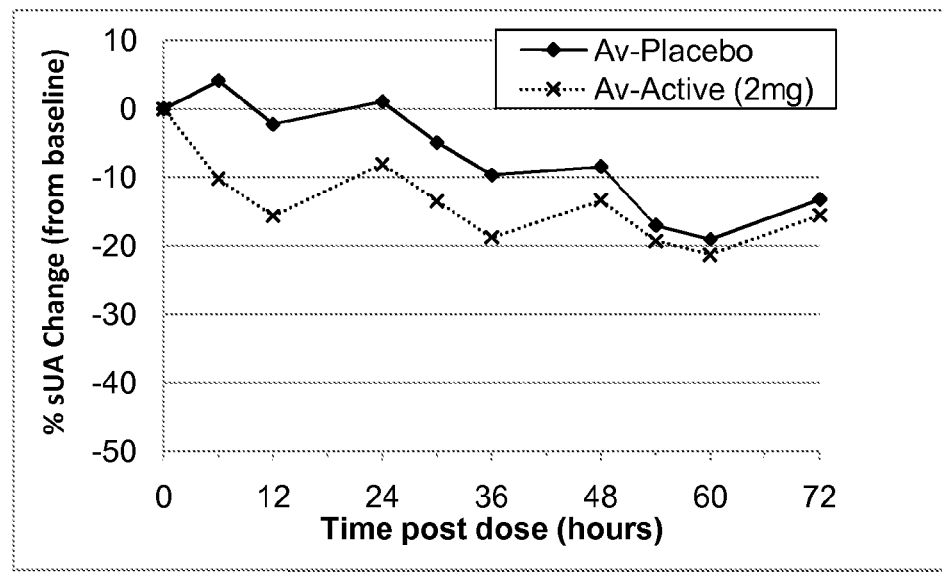
FIG. 2B shows the % serum uric acid change from baseline measured 0-72 hours post-dose for Group 1 (2 mg, fasted). Subjects 1 and 2 received placebo; subjects 3-8 received active.

% sUA change (from baseline) from 0-72 hours post-dose are shown in the table below, and presented in graphical form in FIG. 2B.

| | % sUA change (from baseline) | | | | | | | | | |
|---|---|---|---|---|---|---|---|---|---|---|
| | Subject number | | | | | | | | Mean | Mean |
| Time | 1 | 2 | 3 | 4 | 5 | 6 | 7 | 8 | Placebo | (3-8) |
| 0 | 0 | 0 | 0 | 0 | 0 | 0 | 0 | 0 | 0 | 0 |
| 6 | 6.5 | 2.8 | −30.4 | −47.5 | −35.5 | −37.8 | −38.2 | −33.3 | 4.1 | −10.2 |
| 12 | 0 | 0 | −44.6 | −52.5 | −48.4 | −44.6 | −43.4 | −42.3 | −2.3 | −15.6 |
| 24 | 8.1 | 4.2 | −41.1 | −44.1 | −43.5 | −40.5 | −43.4 | −46.2 | 1.1 | −8.1 |
| 30 | 3.2 | −5.6 | −46.4 | −52.5 | −43.5 | −44.6 | −44.7 | −52.6 | −5.0 | −13.5 |
| 36 | −8.1 | −9.9 | −48.2 | −52.5 | −45.2 | −45.9 | −46.1 | −52.6 | −9.7 | −18.8 |
| 48 | −6.5 | −7 | −32.1 | −42.4 | −38.7 | −36.5 | −35.5 | −48.7 | −8.5 | −13.3 |
| 54 | −1.6 | −14.1 | −33.9 | −45.8 | −37.1 | −27 | −32.9 | −48.7 | −17.0 | −19.3 |
| 60 | −8.1 | −18.3 | −35.7 | −45.8 | −35.5 | −29.7 | −32.9 | −46.2 | −19.1 | −21.3 |
| 72 | 3.2 | −11.3 | −23.2 | −30.5 | −16.1 | −14.9 | −15.8 | −28.2 | −13.3 | −15.5 |

Example 4B: Single-Dose Clinical Trial Results for Group 2

2-((3-(4-cyanonaphthalen-1-yl)pyridin-4-yl)thio)-2-methylpropanoic acid was investigated according to the clinical trial described in Example 3.

Results for the eight subjects in Group 2 (5 mg, fasted) are shown below. Subjects 1 and 2 received placebo; subjects 3-8 received active.

Absolute sUA concentrations (mg/dL) from 0-72 hours post-dose are shown in the table below.

| | Absolute sUA concentration (mg/dL) | | | | | | | | | |
|---|---|---|---|---|---|---|---|---|---|---|
| | Subject | | | | | | | | Mean | Mean |
| Time | 1 | 2 | 3 | 4 | 5 | 6 | 7 | 8 | Placebo | (3-8) |
| 0 | 6.0 | 5.4 | 7.4 | 7.2 | 6.3 | 6.1 | 6.1 | 5.9 | 5.7 | 6.5 |
| 6 | 6.2 | 5.5 | 5.6 | 6.2 | 5.4 | 5.3 | 4.4 | 4.6 | 5.9 | 5.3 |
| 12 | 5.9 | 5.1 | 4.7 | 6.0 | 5.1 | 5.3 | 3.8 | 4.0 | 5.5 | 4.8 |
| 24 | 6.2 | 5.4 | 5.5 | 6.4 | 5.6 | 6.1 | 4.5 | 4.9 | 5.8 | 5.5 |
| 30 | 5.7 | 5.9 | 5.2 | 6.0 | 5.2 | 5.6 | 3.9 | 4.2 | 5.8 | 5.0 |
| 36 | 5.3 | 5.3 | 5.0 | 5.5 | 5.4 | 5.2 | 3.6 | 4.0 | 5.3 | 4.8 |
| 48 | 5.4 | 5.9 | 5.4 | 6.4 | 5.7 | 5.4 | 4.2 | 4.7 | 5.7 | 5.3 |
| 54 | 5.0 | 5.7 | 5.1 | 5.9 | 5.3 | 5.1 | 4.1 | 4.2 | 5.4 | 5.0 |
| 60 | 4.8 | 4.9 | 5.3 | 5.6 | 5.0 | 4.8 | 4.1 | 4.2 | 4.9 | 4.8 |
| 72 | 5.0 | 5.1 | 5.8 | 6.1 | 5.5 | 5.3 | 4.5 | 4.5 | 5.1 | 5.3 |

% sUA change (from baseline) from 0-72 hours post-dose are shown in the table below.

| | % sUA reduction (from baseline) | | | | | | | | | |
|---|---|---|---|---|---|---|---|---|---|---|
| | Subject | | | | | | | | Mean | Mean |
| Time | 1 | 2 | 3 | 4 | 5 | 6 | 7 | 8 | Placebo | (3-8) |
| 0 | 0 | 0 | 0 | 0 | 0 | 0 | 0 | 0 | 0 | 0 |
| 6 | 3.3 | 1.9 | −24.3 | −13.9 | −14.3 | −13.1 | −27.9 | −22.0 | 2.6 | −19.3 |
| 12 | −1.7 | −5.6 | −36.5 | −16.7 | −19.0 | −13.1 | −37.7 | −32.2 | −3.7 | −25.9 |
| 24 | 3.3 | 0.0 | −25.7 | −11.1 | −11.1 | 0.0 | −26.2 | −16.9 | 1.7 | −15.2 |
| 30 | −5.0 | 9.3 | −29.7 | −16.7 | −17.5 | −8.2 | −36.1 | −28.8 | 2.2 | −22.8 |
| 36 | −11.7 | −1.9 | −32.4 | −23.6 | −14.3 | −14.8 | −41.0 | −32.2 | −6.8 | −26.4 |
| 48 | −10.0 | 9.3 | −27.0 | −11.1 | −9.5 | −11.5 | −31.1 | −20.3 | −0.4 | −18.4 |
| 54 | −16.7 | 5.6 | −31.1 | −18.1 | −15.9 | −16.4 | −32.8 | −28.8 | −5.6 | −23.9 |
| 60 | −20.0 | −9.3 | −28.4 | −22.2 | −20.6 | −21.3 | −32.8 | −28.8 | −14.7 | −25.7 |
| 72 | −16.7 | −5.6 | −21.6 | −15.3 | −12.7 | −13.1 | −26.2 | −23.7 | −11.2 | −18.8 |

Example 4C: Single-Dose Clinical Trial Results for Group 3

2-((3-(4-cyanonaphthalen-1-yl)pyridin-4-yl)thio)-2-methylpropanoic acid was investigated according to the clinical trial described in Example 3.

Results for the eight subjects in Group 3 (5 mg, fed) are shown below. Subjects 1 and 2 received placebo; subjects 3-8 received active.

Absolute sUA concentrations (mg/dL) from 0-72 hours post-dose are shown in the table below.

| | Absolute sUA concentration (mg/dL) | | | | | | | | | |
|---|---|---|---|---|---|---|---|---|---|---|
| | Subject | | | | | | | | Mean | Mean |
| Time | 1 | 2 | 3 | 4 | 5 | 6 | 7 | 8 | Placebo | (3-8) |
| 0 | 6.2 | 6.0 | 6.9 | 6.6 | 6.5 | 6.0 | 5.7 | 4.0 | 6.1 | 6.0 |
| 6 | 5.9 | 5.4 | 4.4 | 4.5 | | 4.5 | 4.4 | 2.8 | 5.7 | 4.1 |
| 12 | 5.4 | 5.1 | 4.1 | 4.1 | 4.6 | 4.5 | 4.4 | 2.5 | 5.3 | 4.0 |
| 24 | 6.2 | 5.8 | 5.0 | 5.1 | 5.2 | 5.5 | 5.3 | 3.3 | 6.0 | 4.9 |
| 30 | 5.6 | 5.3 | 4.6 | 4.6 | 4.7 | 5.1 | 4.7 | 2.8 | 5.5 | 4.4 |
| 36 | 5.3 | 5.0 | 4.3 | 4.4 | 4.6 | 4.9 | 4.5 | 2.6 | 5.2 | 4.2 |
| 48 | 5.6 | 4.6 | 4.7 | 4.6 | 5.0 | 4.6 | 4.9 | 2.9 | 5.1 | 4.5 |
| 54 | 5.0 | 5.0 | 4.3 | 3.5 | 4.7 | 3.7 | 4.5 | 2.7 | 5.0 | 3.9 |
| 60 | 4.9 | 4.6 | 5.0 | 4.7 | 4.5 | 4.8 | 4.3 | 2.6 | 4.8 | 4.3 |
| 72 | 5.4 | 4.8 | 5.9 | 5.4 | 5.2 | 5.3 | 4.8 | 3.0 | 5.1 | 4.9 |

% sUA change (from baseline) from 0-72 hours post-dose are shown in the table below.

| % sUA reduction (from baseline) | | | | | | | | | | |
|---|---|---|---|---|---|---|---|---|---|---|
| | Subject | | | | | | | | Mean | Mean |
| Time | 1 | 2 | 3 | 4 | 5 | 6 | 7 | 8 | Placebo | (3-8) |
| 0 | 0 | 0 | 0 | 0 | 0 | 0 | 0 | 0 | 0 | 0 |
| 6 | -4.8 | -10.0 | -36.2 | -31.8 | | -25.0 | -22.8 | -30.0 | -7.4 | -29.2 |
| 12 | -12.9 | -15.0 | -40.6 | -37.9 | -29.2 | -25.0 | -22.8 | -37.5 | -14.0 | -32.2 |
| 24 | 0.0 | -3.3 | -27.5 | -22.7 | -20.0 | -8.3 | -7.0 | -17.5 | -1.7 | -17.2 |
| 30 | -9.7 | -11.7 | -33.3 | -30.3 | -27.7 | -15.0 | -17.5 | -30.0 | -10.7 | -25.6 |
| 36 | -14.5 | -16.7 | -37.7 | -33.3 | -29.2 | -18.3 | -21.1 | -35.0 | -15.6 | -29.1 |
| 48 | -9.7 | -23.3 | -31.9 | -30.3 | -23.1 | -23.3 | -14.0 | -27.5 | -16.5 | -25.0 |
| 54 | -19.4 | -16.7 | -37.7 | -47.0 | -27.7 | -38.3 | -21.1 | -32.5 | -18.1 | -34.1 |
| 60 | -21.0 | -23.3 | -27.5 | -28.8 | -30.8 | -20.0 | -24.6 | -35.0 | -22.2 | -27.8 |
| 72 | -12.9 | -20.0 | -14.5 | -18.2 | -20.0 | -11.7 | -15.8 | -25.0 | -16.5 | -17.5 |

Figure 3A:
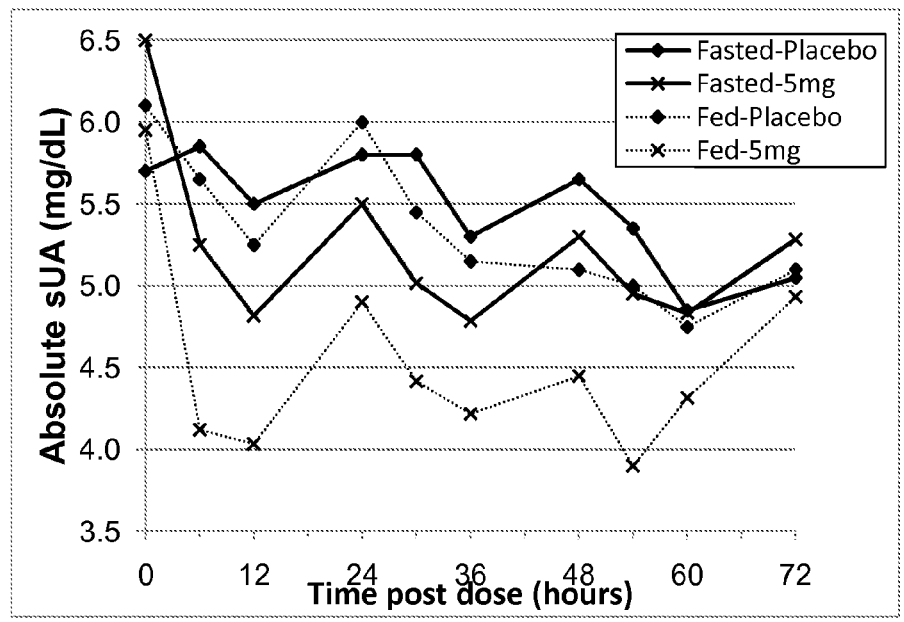
FIG. 3A shows the absolute serum uric acid concentrations (mg/dL) measured 0-72 hours post-dose for Group 2 (5 mg, fasted). Subjects 1 and 2 received placebo; subjects 3-8 received active.
Figure 3B:
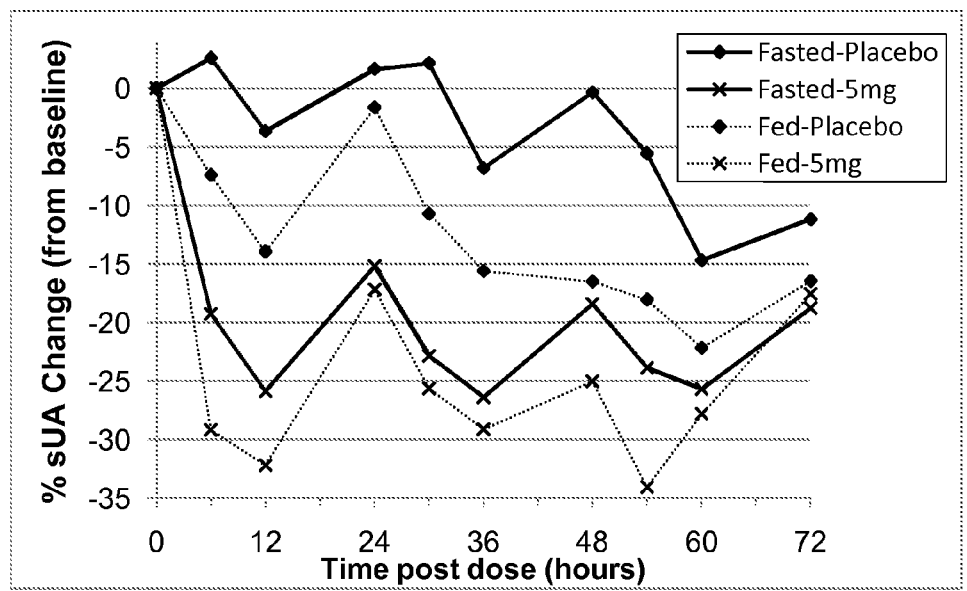
FIG. 3B shows the % serum uric acid change from baseline measured 0-72 hours post-dose for Groups 2 and 3 (5 mg, fasted and fed respectively). Subjects 1 and 2 received placebo; subjects 3-8 received active.

Absolute sUA (mg/dL) and % sUA change from 0-72 hours post-dose for groups 2 and 3, are presented in graphical form in FIGS. 3A and 3B respectively.

Example 4D: Single-Dose Clinical Trial Results for Group 4

2-((3-(4-cyanonaphthalen-1-yl)pyridin-4-yl)thio)-2-methylpropanoic acid was investigated according to the clinical trial described in Example 3.

Results for the eight subjects in Group 4 (20 mg, fasted) are shown below. Subjects 1 and 2 received placebo; subjects 3-8 received active.

Absolute sUA concentrations (mg/dL) from 0-72 hours post-dose are shown in the table below.

| Absolute sUA concentration (mg/dL) | | | | | | | | | | |
|---|---|---|---|---|---|---|---|---|---|---|
| | Subject | | | | | | | | Mean | Mean |
| Time | 1 | 2 | 3 | 4 | 5 | 6 | 7 | 8 | Placebo | (3-8) |
| 0 | 7.1 | 6.2 | 7.8 | 7.6 | 7.4 | 6.2 | 5.9 | 5.6 | 6.7 | 6.8 |
| 6 | 7.3 | 6.6 | 5.2 | 4.7 | 4.6 | 4.0 | 3.1 | 3.9 | 7.0 | 4.3 |
| 12 | 7.1 | 4.1 | 4.5 | 4.3 | 6.2 | 3.2 | 2.8 | 3.1 | 5.6 | 4.0 |
| 24 | 7.4 | 6.7 | 4.2 | 4.3 | 4.4 | 3.5 | 3.3 | 3.3 | 7.1 | 3.8 |
| 30 | 6.7 | 6.4 | 3.7 | 4.2 | 4.1 | 3.5 | 2.8 | 3.0 | 6.6 | 3.6 |
| 36 | 6.4 | 5.7 | 3.7 | 4.1 | 4.0 | 3.4 | 2.8 | 2.9 | 6.1 | 3.5 |
| 48 | 6.6 | 5.8 | 4.0 | 4.9 | 4.7 | 3.8 | 3.4 | 3.8 | 6.2 | 4.1 |
| 54 | 6.1 | 6.1 | 4.0 | 5.1 | 5.4 | 3.9 | 3.2 | 3.7 | 6.1 | 4.2 |
| 60 | 5.8 | 5.7 | 4.2 | 5.1 | 5.2 | 4.0 | 3.2 | 3.6 | 5.8 | 4.2 |
| 72 | 6.3 | 6.4 | 5.6 | 6.4 | 6.3 | 5.2 | 4.1 | 4.3 | 6.4 | 5.3 |

% sUA change (from baseline) from 0-72 hours post-dose are shown in the table below.

| % sUA reduction (from baseline) | | | | | | | | | | |
|---|---|---|---|---|---|---|---|---|---|---|
| | Subject | | | | | | | | Mean | Mean |
| Time | 1 | 2 | 3 | 4 | 5 | 6 | 7 | 8 | Placebo | (3-8) |
| 0 | 0 | 0 | 0 | 0 | 0 | 0 | 0 | 0 | 0 | 0 |
| 6 | 2.8 | 6.5 | -33.3 | -38.2 | -37.8 | -35.5 | -47.5 | -30.4 | 4.7 | -37.1 |
| 12 | 0.0 | -33.9 | -42.3 | -43.4 | -16.2 | -48.4 | -52.5 | -44.6 | -17.0 | -41.2 |
| 24 | 4.2 | 8.1 | -46.2 | -43.4 | -40.5 | -43.5 | -44.1 | -41.1 | 6.2 | -43.1 |
| 30 | -5.6 | 3.2 | -52.6 | -44.7 | -44.6 | -43.5 | -52.5 | -46.4 | -1.2 | -47.4 |
| 36 | -9.9 | -8.1 | -52.6 | -46.1 | -45.9 | -45.2 | -52.5 | -48.2 | -9.0 | -48.4 |
| 48 | -7.0 | -6.5 | -48.7 | -35.5 | -36.5 | -38.7 | -42.4 | -32.1 | -6.8 | -39.0 |
| 54 | -14.1 | -1.6 | -48.7 | -32.9 | -27.0 | -37.1 | -45.8 | -33.9 | -7.9 | -37.6 |
| 60 | -18.3 | -8.1 | -46.2 | -32.9 | -29.7 | -35.5 | -45.8 | -35.7 | -13.2 | -37.6 |
| 72 | -11.3 | 3.2 | -28.2 | -15.8 | -14.9 | -16.1 | -30.5 | -23.2 | -4.1 | -21.5 |

Example 4E: Single-Dose Clinical Trial Results for Group 5

2-((3-(4-cyanonaphthalen-1-yl)pyridin-4-yl)thio)-2-methylpropanoic acid was investigated according to the clinical trial described in Example 3.

Results for the eight subjects in Group 5 (20 mg, fed) are shown below. Subjects 1 and 2 received placebo; subjects 3-8 received active.

Absolute sUA concentrations (mg/dL) from 0-72 hours post-dose are shown in the table below.

| Absolute sUA concentration (mg/dL) | | | | | | | | | | |
|---|---|---|---|---|---|---|---|---|---|---|
| | Subject | | | | | | | | Mean | Mean |
| Time | 1 | 2 | 3 | 4 | 5 | 6 | 7 | 8 | Placebo | (3-8) |
| 0 | 6.7 | 5.6 | 8.1 | 7.8 | 7.6 | 6.4 | 6.3 | 6.1 | 6.2 | 7.1 |
| 6 | 6.4 | 5.4 | 5.0 | 4.2 | 3.5 | 3.6 | 3.6 | 3.5 | 5.9 | 3.9 |
| 12 | 6.0 | 5.1 | 4.0 | 3.7 | 2.4 | 2.5 | 3.0 | 2.8 | 5.6 | 3.1 |
| 24 | 7.0 | 5.6 | 4.5 | 4.6 | 3.1 | 3.2 | 3.5 | 3.8 | 6.3 | 3.8 |
| 30 | 6.3 | 5.1 | 4.3 | 4.2 | 3.3 | 3.0 | 3.2 | 3.9 | 5.7 | 3.7 |
| 36 | 6.0 | 4.8 | 4.1 | 4.0 | 3.3 | 3.0 | 3.0 | 3.7 | 5.4 | 3.5 |
| 48 | 6.5 | 5.1 | 4.8 | 4.8 | 4.7 | 3.7 | 3.6 | 4.7 | 5.8 | 4.4 |
| 54 | 6.1 | 4.8 | 4.6 | 4.8 | 4.7 | 3.7 | 3.6 | 4.4 | 5.5 | 4.3 |
| 60 | 5.6 | 4.5 | 4.5 | 4.7 | 4.7 | 3.5 | 3.5 | 4.3 | 5.1 | 4.2 |
| 72 | 6.0 | 4.9 | 5.3 | 5.5 | 5.6 | 4.5 | 4.2 | 5.0 | 5.5 | 5.0 |

% sUA change (from baseline) from 0-72 hours post-dose are shown in the table below.

| | % sUA reduction (from baseline) | | | | | | | | | |
|---|---|---|---|---|---|---|---|---|---|---|
| | Subject | | | | | | | | Mean | Mean |
| Time | 1 | 2 | 3 | 4 | 5 | 6 | 7 | 8 | Placebo | (3-8) |
| 0 | 0 | 0 | 0 | 0 | 0 | 0 | 0 | 0 | 0 | 0 |
| 6 | −4.5 | −3.6 | −38.3 | −46.2 | −53.9 | −43.8 | −42.9 | −42.6 | −4.05 | −44.6 |
| 12 | −10.4 | −8.9 | −50.6 | −52.6 | −68.4 | −60.9 | −52.4 | −54.1 | −9.65 | −56.5 |
| 24 | 4.5 | 0.0 | −44.4 | −41.0 | −59.2 | −50.0 | −44.4 | −37.7 | 2.25 | −46.1 |
| 30 | −6.0 | −8.9 | −46.9 | −46.2 | −56.6 | −53.1 | −49.2 | −36.1 | −7.45 | −48 |
| 36 | −10.4 | −14.3 | −49.4 | −48.7 | −56.6 | −53.1 | −52.4 | −39.3 | −12.4 | −49.9 |
| 48 | −3.0 | −8.9 | −40.7 | −38.5 | −38.2 | −42.2 | −42.9 | −23.0 | −5.95 | −37.6 |
| 54 | −9.0 | −14.3 | −43.2 | −38.5 | −38.2 | −42.2 | −42.9 | −27.9 | −11.7 | −38.8 |
| 60 | −16.4 | −19.6 | −44.4 | −39.7 | −38.2 | −45.3 | −44.4 | −29.5 | −18 | −40.3 |
| 72 | −10.4 | −12.5 | −34.6 | −29.5 | −26.3 | −29.7 | −33.3 | −18.0 | −11.5 | −28.6 |

Figure 4A:
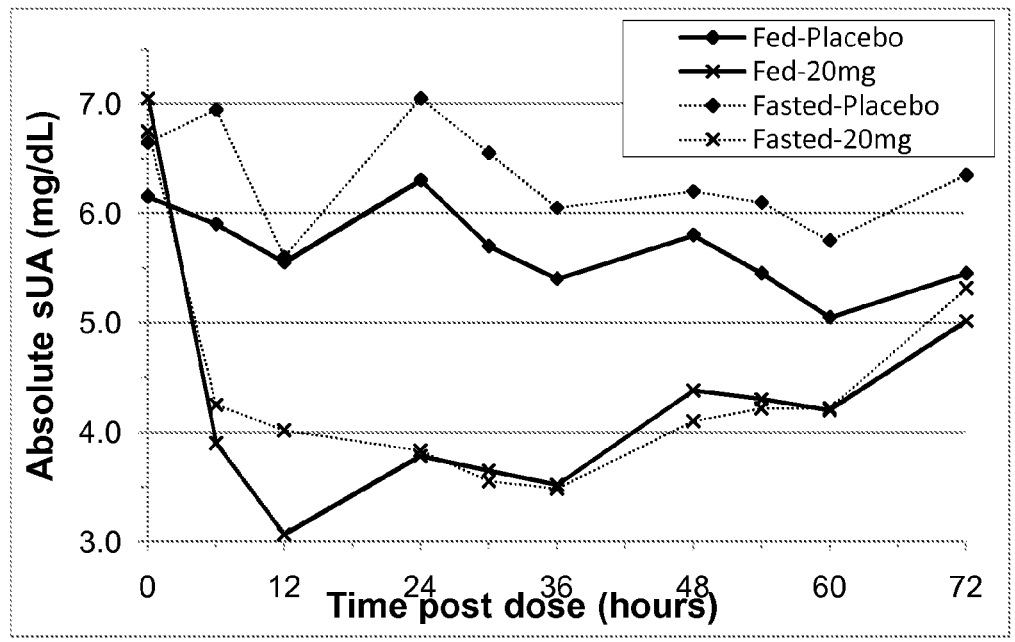
FIG. 4A shows the absolute serum uric acid concentrations (mg/dL) measured 0-72 hours post-dose for Groups 4 and 5 (20 mg, fasted and fed respectively). Subjects 1 and 2 received placebo; subjects 3-8 received active.
Figure 4B:
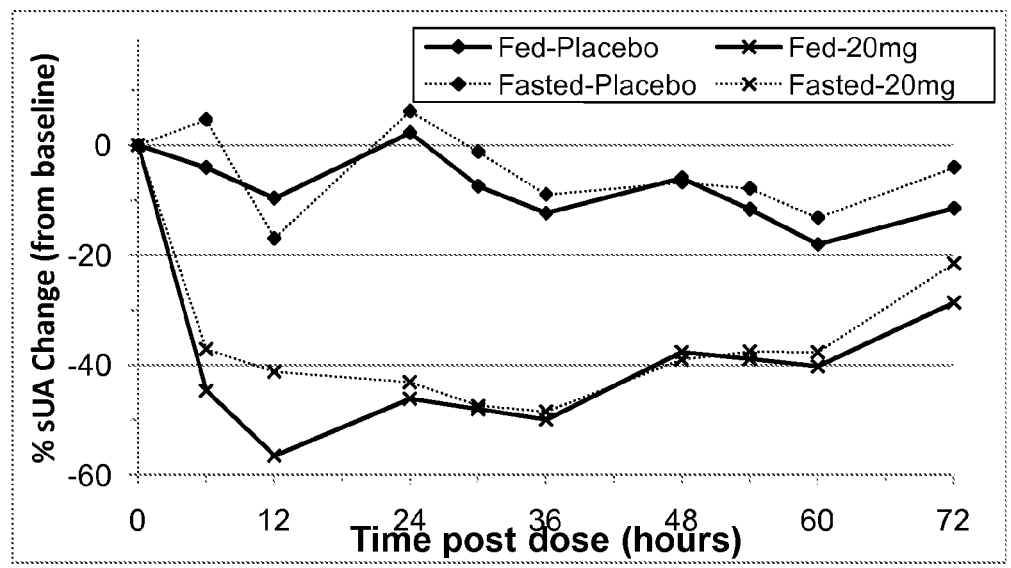
FIG. 4B shows the % serum uric acid change from baseline measured 0-72 hours post-dose for Groups 4 and 5 (20 mg, fasted and fed respectively). Subjects 1 and 2 received placebo; subjects 3-8 received active.

Absolute sUA (mg/dL) and % sUA change from 0-72 hours post-dose for groups 4 and 5, are presented in graphical form in FIGS. 4A and 4B respectively.

Example 4F: Single-Dose Clinical Trial Results for Group 6

2-((3-(4-cyanonaphthalen-1-yl)pyridin-4-yl)thio)-2-methylpropanoic acid was investigated according to the clinical trial described in Example 3.

Results for the eight subjects in Group 6 (40 mg, fasted) are shown below. Subjects 1 and 2 received placebo; subjects 3-8 received active.

Figure 5A:
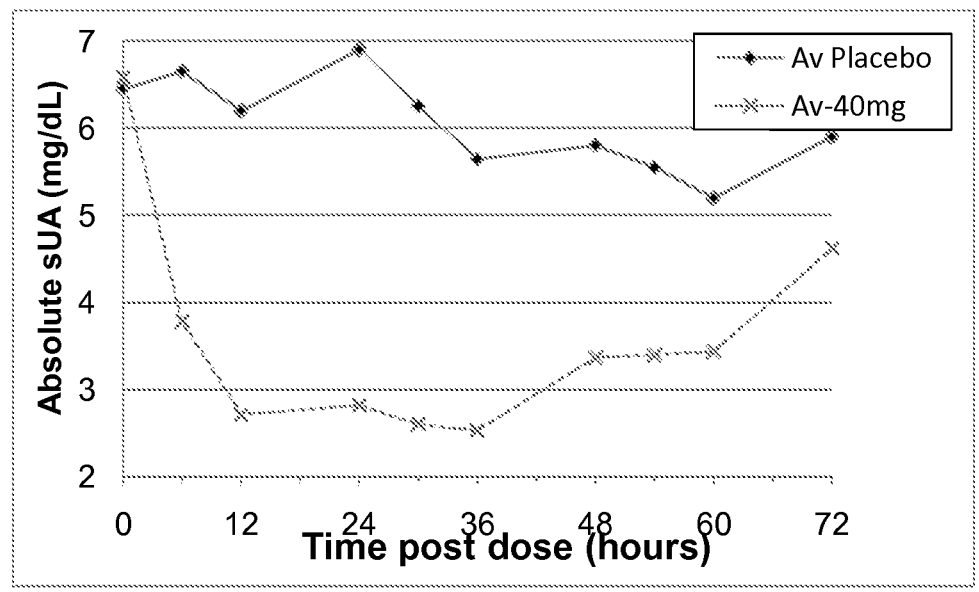
FIG. 5A shows the absolute serum uric acid concentrations (mg/dL) measured 0-72 hours post-dose for Group 6 (40 mg, fasted). Subjects 1 and 2 received placebo; subjects 3-8 received active.

Absolute sUA concentrations (mg/dL) from 0-72 hours post-dose are shown in the table below, and presented in graphical form in FIG. 5A.

| | Absolute sUA concentration (mg/dL) | | | | | | | | | |
|---|---|---|---|---|---|---|---|---|---|---|
| | Subject number | | | | | | | | Mean | Mean |
| Time | 1 | 2 | 3 | 4 | 5 | 6 | 7 | 8 | Placebo | (3-8) |
| 0 | 6.9 | 6.0 | 7.6 | 7.4 | 6.8 | 6.1 | 5.9 | 5.7 | 6.5 | 6.6 |
| 6 | 7.2 | 6.1 | 5.8 | 3.6 | 4.2 | 2.8 | 3.0 | 3.3 | 6.7 | 3.8 |
| 12 | 6.7 | 5.7 | 4.5 | 2.3 | 3.2 | 2.2 | 1.8 | 2.3 | 6.2 | 2.7 |
| 24 | 7.4 | 6.4 | 4.0 | 2.7 | 3.3 | 2.7 | 1.7 | 2.5 | 6.9 | 2.8 |
| 30 | 6.7 | 5.8 | 3.5 | 2.5 | 2.8 | 2.7 | 1.5 | 2.6 | 6.3 | 2.6 |
| 36 | 5.9 | 5.4 | 3.1 | 2.5 | 2.7 | 2.7 | 1.5 | 2.7 | 5.7 | 2.5 |
| 48 | 5.9 | 5.7 | 3.5 | 3.7 | 3.5 | 3.8 | 2.6 | 3.1 | 5.8 | 3.4 |
| 54 | 5.8 | 5.3 | 3.3 | 3.9 | 3.4 | 3.7 | 2.7 | 3.4 | 5.6 | 3.4 |
| 60 | 5.5 | 4.9 | 3.3 | 3.7 | 3.5 | 3.7 | 2.8 | 3.6 | 5.2 | 3.4 |
| 72 | 6.5 | 5.3 | 4.5 | 5.1 | 4.5 | 4.9 | 4.1 | 4.6 | 5.9 | 4.6 |

Figure 5B:
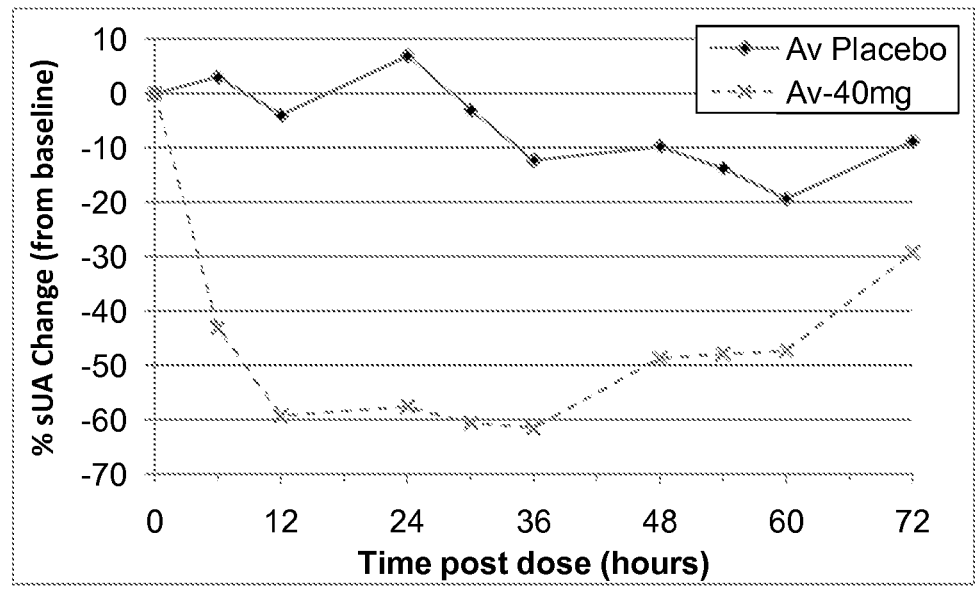
FIG. 5B shows the % serum uric acid change from baseline measured 0-72 hours post-dose for Group 6 (40 mg, fasted). Subjects 1 and 2 received placebo; subjects 3-8 received active.

% sUA change (from baseline) from 0-72 hours post-dose are shown in the table below, and presented in graphical form in FIG. 5B.

| | % sUA change (from baseline) | | | | | | | | | |
|---|---|---|---|---|---|---|---|---|---|---|
| | Subject number | | | | | | | | Mean | Mean |
| Time | 1 | 2 | 3 | 4 | 5 | 6 | 7 | 8 | Placebo | (3-8) |
| 0 | 0 | 0 | 0 | 0 | 0 | 0 | 0 | 0 | 0 | 0 |
| 6 | 4.3 | 1.7 | −23.7 | −51.4 | −38.2 | −54.1 | −49.2 | −42.1 | 3.0 | −43.1 |
| 12 | −2.9 | −5.0 | −40.8 | −68.9 | −52.9 | −63.9 | −69.5 | −59.6 | −4.0 | −59.3 |
| 24 | 7.2 | 6.7 | −47.4 | −63.5 | −51.5 | −55.7 | −71.2 | −56.1 | 7.0 | −57.6 |
| 30 | −2.9 | −3.3 | −53.9 | −66.2 | −58.8 | −55.7 | −74.6 | −54.4 | −3.1 | −60.6 |
| 36 | −14.5 | −10.0 | −59.2 | −66.2 | −60.3 | −55.7 | −74.6 | −52.6 | −12.3 | −61.4 |
| 48 | −14.5 | −5.0 | −53.9 | −50.0 | −48.5 | −37.7 | −55.9 | −45.6 | −9.8 | −48.6 |
| 54 | −15.9 | −11.7 | −56.6 | −47.3 | −50.0 | −39.3 | −54.2 | −40.4 | −13.8 | −48.0 |
| 60 | −20.3 | −18.3 | −56.6 | −50.0 | −48.5 | −39.3 | −52.5 | −36.8 | −19.3 | −47.3 |
| 72 | −5.8 | −11.7 | −40.8 | −31.1 | −33.8 | −19.7 | −30.5 | −19.3 | −8.8 | −29.2 |

Figure 6A:
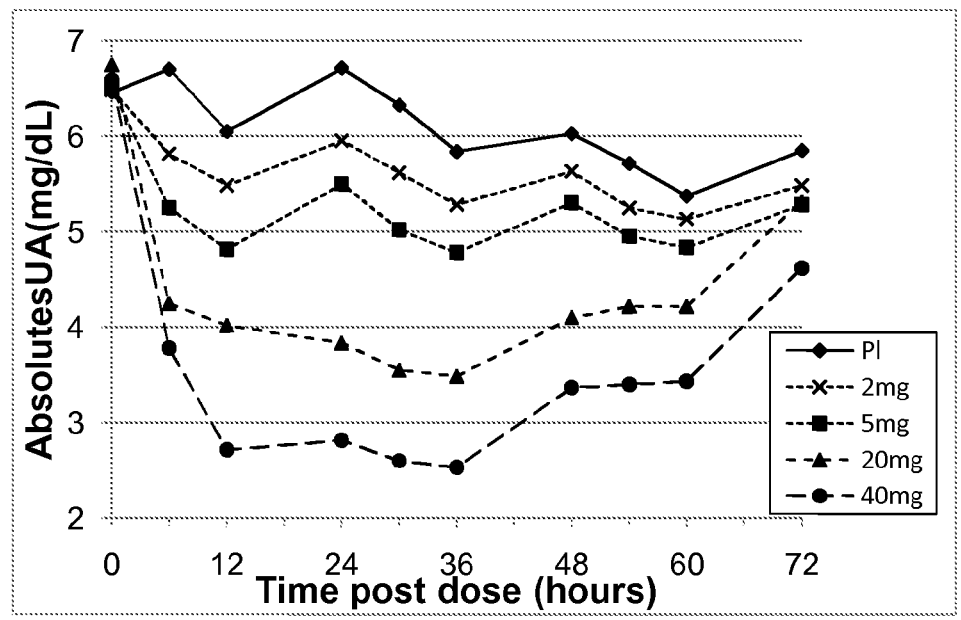
FIG. 6A shows the absolute serum uric acid concentrations (mg/dL) measured 0-72 hours post-dose for Groups 1, 2, 4 and 6 (2 mg, 5 mg, 20 mg and 40 mg respectively, all fasted).
Figure 6B:
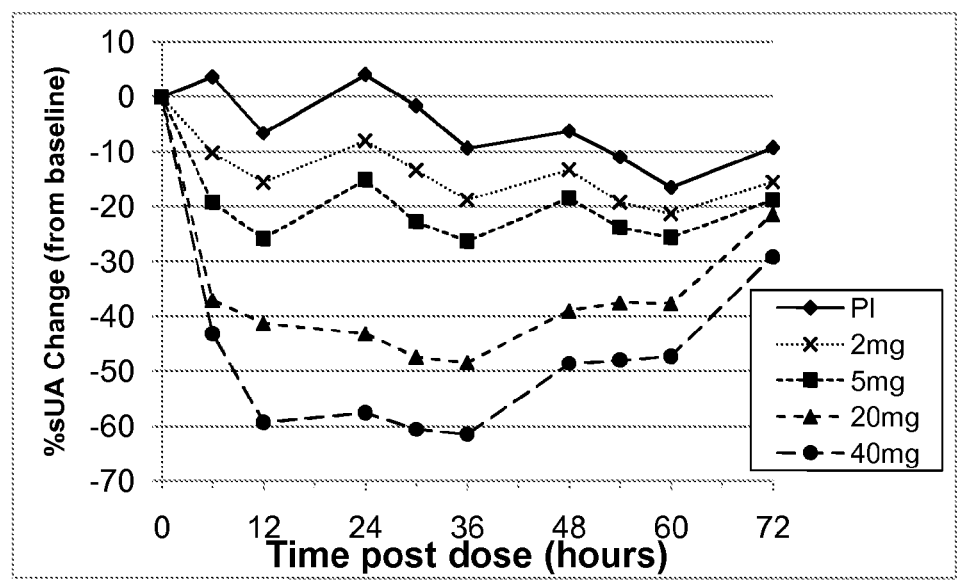
FIG. 6B shows the % serum uric acid change from baseline measured 0-72 hours post-dose for Groups 1, 2, 4 and 6 (2 mg, 5 mg, 20 mg and 40 mg respectively, all fasted).

Absolute sUA and % sUA change from 0-72 hours post-dose for groups 1, 2, 4 and 6 (2 mg, 5 mg, 20 mg and 40 mg, all fasted) are presented in graphical form in FIGS. 6A and 6B, respectively.

Example 5: Multi-Dose Phase I Clinical Trial 2-((3-(4-cyanonaphthalen-1-yl)pyridin-4-yl)thio)-2-methylpropanoic acid was investigated according to the clinical trial described below.

Study

A Phase 1, Randomized, Double-Blind, Placebo-Controlled Study to Evaluate Safety, Tolerability, Pharmacokinetics and Preliminary Food Effect of Multiple Rising Doses of a URAT1 Inhibitor, in Healthy Adult Male Volunteers.

Investigational Plan/Study Design

Fasted subjects receive oral doses of active or placebo, once daily, for 10 days, at the following doses:
Group 7: 1 mg
Group 8: 5 mg
Group 9: 10 mg Study Details Subjects 36 subjects in 3 dose groups, 12 subjects/group, are randomized 4:1 to receive active (9/group) or placebo (2/group). All study procedures are the same regardless of whether subject receives active or placebo. Total duration of subject participation, including screening period, is ~2-4 weeks, and the total volume of blood collected from each subject during the entire study <500 mL, (less than typically collected during a volunteer blood donation).

Study Medication 5 mg, active and placebo, tablets packaged in 35 count HDPE bottles, stored at controlled room temperature (15-30° C.). Placebo tablets are designed to match the active tablets—identical size, form, taste, and color, and containing the same excipients. 1 mg doses were administered as oral solutions.

Participation Criteria

Inclusion Criteria:

Healthy male adults, age 18-45, with body weight >50 kg and BMI 18-30 kg/m².

All laboratory parameters (chemistry, hematology, urinalysis) within normal limits; sUA≥5 mg/dL.

Subjects free of clinically significant disease and have normal physical examination, including normal blood pressure (90-140/50-90 mmHg), heart rate (50-100 bpm), body temp (35.0-37.5° C.) and respiratory rate (8-20 bpm), and no electrocardiogram abnormalities.

Exclusion Criteria:

Any illness within 1 week of dosing, or HIV, Hep B or Hep C positive.

History of kidney stones, significant metabolic, hematological, pulmonary, cardiovascular, gastrointestinal, neurologic, hepatic, renal, urological, psychiatric disorders, cardiac abnormalities, or major surgery within past 3 months.

Donation of blood or plasma, or received an investigational therapy within previous 3 months.

Any drug treatment, including prescribed/OTC medicines or herbal preparations, in previous 14 days.

History of drug addiction, excessive alcohol use, heavy caffeine drinker, use of tobacco products within previous 30 days, and/or refusal to abstain from tobacco, alcohol, caffeine during the study.

Refusal to refrain from strenuous exercise during study.

Subjects with allergies, or hypersensitivity to any ingredient in the investigational products.

Summary of Study Activities/Schedule of Events

Figure 1B:
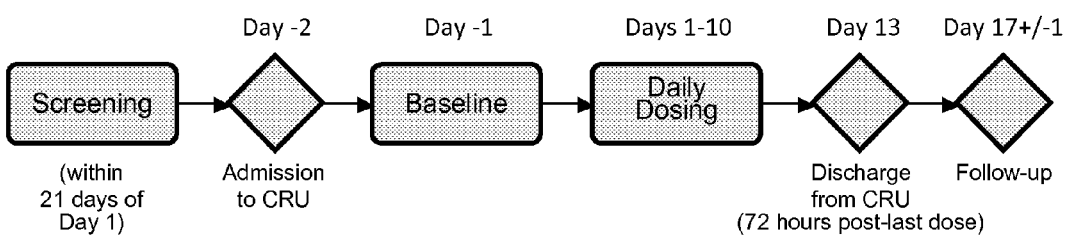
FIG. 1B shows a schematic representation of schedule of events during the trial described in Example 5.

FIG. 1B shows a schematic representation of the schedule of events.

Screening Visit Days −21 to −3

After obtaining written informed consent, subjects screened to confirm study eligibility.

Pretreatment: Day −2 to −1

Subjects admitted to CRU ~48 hours prior to dosing and remain at the center until all study assessments complete, with standardized meals served at appropriate times.

Urine, serum and plasma samples collected Day −1 beginning 24 hours pre-dose.

Treatment Period: Days 1 to 13

The following performed during the treatment period:

Subjects dosed in the morning of Days 1-10 with ~240 mL of room temp water.

Urine, serum and plasma samples collected periodically

PD samples frozen (−20° C.) and stored; all samples from a given subject assayed in a single analytical run.

End of Study

Subjects remain at the study site until all scheduled samples are collected through the morning of Day 13. Upon completion of all study-related procedures and assessments, subjects discharged.

Subjects return to study site for follow-up visit on Day 17±1, for physical exam, vital signs, ECG, safety laboratory tests, AEs and concomitant medications.

Adverse Events, Serious Adverse Events and Removal from the Trail

An adverse event (AE) is any untoward medical occurrence associated with the use of a drug, whether or not considered drug related. Adverse events are continuously monitored throughout the study.

The severity of AEs should be identified as mild, moderate, severe or life threatening. The relationship of the AE to the study medication should be identified as Not Related, Unlikely, or Possible.

A serious adverse event (SAE) is any AE that results in: death, life-threatening AE, hospitalization, a persistent or significant disability/incapacity or substantial disruption of the ability to conduct normal life functions, or a congenital anomaly/birth defect.

A subject may be withdrawn for a protocol violation, a serious AE, a clinically significant change in a laboratory parameter or at the request of the subject. Subjects withdrawing after dosing not replaced.

Evaluation of Results

Pharmacokinetics (PK), Pharmacodynamics (PD) and Safety & Adverse Events are evaluated. All dosed subjects who have evaluable PK data make up the PK Population. All dosed subjects make up the Safety Population. All sampling times are in relation to the beginning of dosing (subject taking first tablet).

Example 6A: Multi-Dose Clinical Trial Results for Group 7

2-((3-(4-cyanonaphthalen-1-yl)pyridin-4-yl)thio)-2-methylpropanoic acid was evaluated according to the clinical trial described above in Example 5.

Results for twelve subjects in group 7, receiving 1 mg active or placebo, once daily for 10 days, are shown below. Subjects 1, 2 and 3 received placebo; subjects 4-12 received active.

Figure 7A:
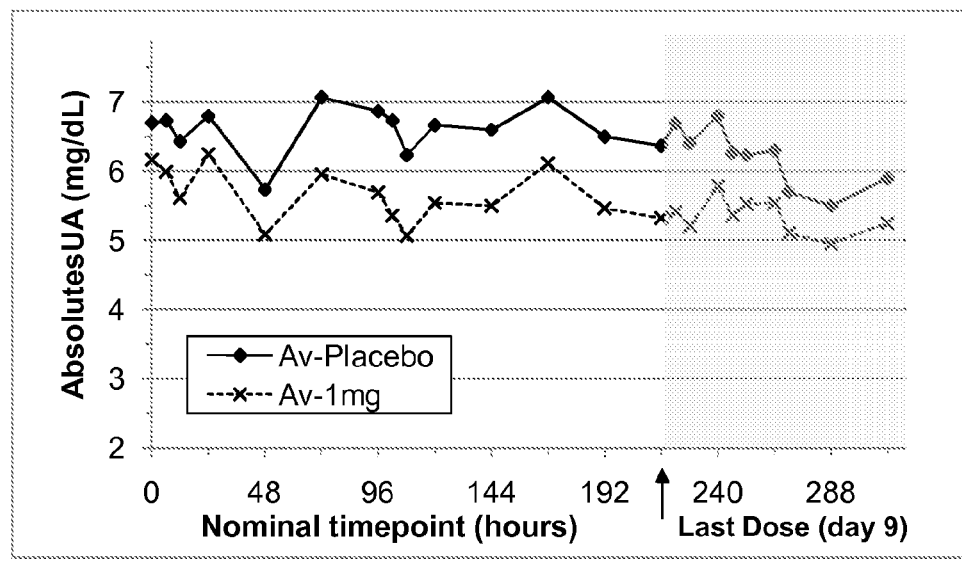
FIG. 7A shows the absolute serum uric acid concentrations (mg/dL; mean placebo-subjects 1, 2 and 3; and mean active-subjects 4-12), measured at nominal timepoints (days 0-9—once daily dosing, plus days 10-13, post dosing) for twelve subjects in group 7 (1 mg, once daily for 10 days), as described in example 6A.

Absolute sUA concentrations (mg/dL) by nominal timepoint (i.e. days 0-9—once daily dosing, plus days 10-13, post dosing) are shown in the table below, and presented in graphical form in FIG. 7A.

| | Absolute sUA concentration (mg/dL) | | | | | | | | | | | | | |
|---|---|---|---|---|---|---|---|---|---|---|---|---|---|---|
| | Subject Number | | | | | | | | | | | | Mean | Mean |
| Time | 1 | 2 | 3 | 4 | 5 | 6 | 7 | 8 | 9 | 10 | 11 | 12 | Placebo | (4-12) |
| 0 | 7.3 | 6.6 | 6.2 | 7.0 | 6.9 | 6.7 | 6.2 | 6.0 | 5.9 | 5.8 | 5.6 | 5.4 | 6.7 | 6.2 |
| 6 | 7.3 | 6.5 | 6.4 | 6.9 | 6.8 | 6.7 | 6.2 | 5.3 | 5.8 | 5.5 | 5.5 | 5.2 | 6.7 | 6.0 |
| 12 | 7.1 | 6.1 | 6.1 | 6.6 | 6.4 | 6.1 | 6.1 | 5.0 | 5.3 | 5.1 | 5.0 | 4.9 | 6.4 | 5.6 |
| 24 | 7.4 | 6.9 | 6.1 | 7.1 | 6.6 | 6.8 | 6.7 | 5.8 | 6.0 | 5.8 | 5.9 | 5.5 | 6.8 | 6.2 |
| 48 | 7.0 | 5.8 | 4.4 | 6.0 | 5.8 | 5.4 | 5.5 | 4.7 | 4.9 | 5.1 | 3.6 | 4.8 | 5.7 | 5.1 |
| 72 | 7.9 | 6.8 | 6.5 | 7.0 | 6.6 | 6.2 | 6.2 | 5.5 | 5.9 | 5.3 | 5.6 | 5.3 | 7.1 | 6.0 |
| 96 | 7.9 | 6.5 | 6.2 | 6.7 | 6.7 | 6.1 | 6.0 | 5.0 | 5.5 | 5.0 | 5.1 | 5.1 | 6.9 | 5.7 |
| 102 | 7.7 | 6.3 | 6.2 | 6.2 | 6.2 | 5.9 | 5.7 | 4.6 | 5.4 | 4.4 | 4.9 | 4.9 | 6.7 | 5.4 |
| 108 | 7.3 | 5.9 | 5.5 | 6.1 | 5.9 | 5.4 | 5.6 | 4.3 | 5.0 | 4.1 | 4.4 | 4.8 | 6.2 | 5.1 |
| 120 | 7.7 | 6.2 | 6.1 | 6.6 | 6.2 | 6.2 | 5.8 | 5.0 | 5.6 | 4.6 | 5.0 | 4.9 | 6.7 | 5.5 |
| 144 | 7.6 | 6.3 | 5.9 | 6.5 | 6.2 | 6.1 | 5.8 | 5.0 | 5.5 | 4.6 | 5.0 | 4.8 | 6.6 | 5.5 |
| 168 | 8.0 | 6.6 | 6.6 | 7.2 | 6.8 | 6.3 | 6.5 | 5.4 | 6.2 | 5.2 | 5.8 | 5.6 | 7.1 | 6.1 |
| 192 | 7.4 | 6.1 | 6.0 | 6.5 | 6.1 | 5.9 | 5.6 | 5.1 | 5.5 | 4.6 | 5.0 | 4.9 | 6.5 | 5.5 |
| 216 | 7.5 | 6.0 | 5.6 | 6.1 | 5.8 | 5.3 | 5.6 | 4.9 | 5.9 | 4.7 | 4.9 | 4.7 | 6.4 | 5.3 |
| 222 | 7.7 | 6.3 | 6.1 | 6.3 | 5.9 | 5.8 | 5.4 | 5.0 | 5.5 | 4.7 | 5.2 | 4.9 | 6.7 | 5.4 |
| 228 | 7.4 | 6.1 | 5.7 | 6.2 | 5.6 | 5.5 | 5.3 | 4.8 | 5.4 | 4.3 | 4.8 | 4.9 | 6.4 | 5.2 |
| 240 | 7.8 | 6.7 | 5.9 | 6.9 | 6.2 | 6.2 | 5.9 | 5.2 | 6.0 | 4.8 | 5.5 | 5.3 | 6.8 | 5.8 |
| 246 | 7.3 | 6.1 | 5.4 | 6.4 | 5.8 | 5.6 | 5.7 | 5.1 | 5.5 | 4.4 | 4.8 | 4.9 | 6.3 | 5.4 |
| 252 | 7.3 | 5.8 | 5.6 | 6.9 | 6.1 | 5.9 | 5.9 | 5.0 | 5.4 | 4.5 | 5.0 | 5.0 | 6.2 | 5.5 |
| 264 | 7.5 | 5.8 | 5.6 | 6.4 | 6.2 | 6.0 | 5.7 | 5.1 | 5.7 | 4.5 | 5.1 | 5.1 | 6.3 | 5.5 |
| 270 | 6.9 | 5.1 | 5.1 | 6.0 | 5.9 | 5.4 | 5.3 | 4.7 | 5.1 | 4.1 | 4.6 | 4.8 | 5.7 | 5.1 |
| 288 | 6.6 | 4.9 | 5.0 | 6.0 | 5.8 | 5.4 | 5.2 | 4.4 | 4.9 | 3.9 | 4.5 | 4.5 | 5.5 | 5.0 |
| 312 | 6.9 | 5.4 | 5.4 | 6.2 | 6.1 | 5.6 | 5.4 | 4.9 | 5.4 | 4.4 | 4.7 | 4.6 | 5.9 | 5.3 |

Timepoint in bold = dosing timepoints
Timepoints 222 and greater = post dosing

Figure 7B:
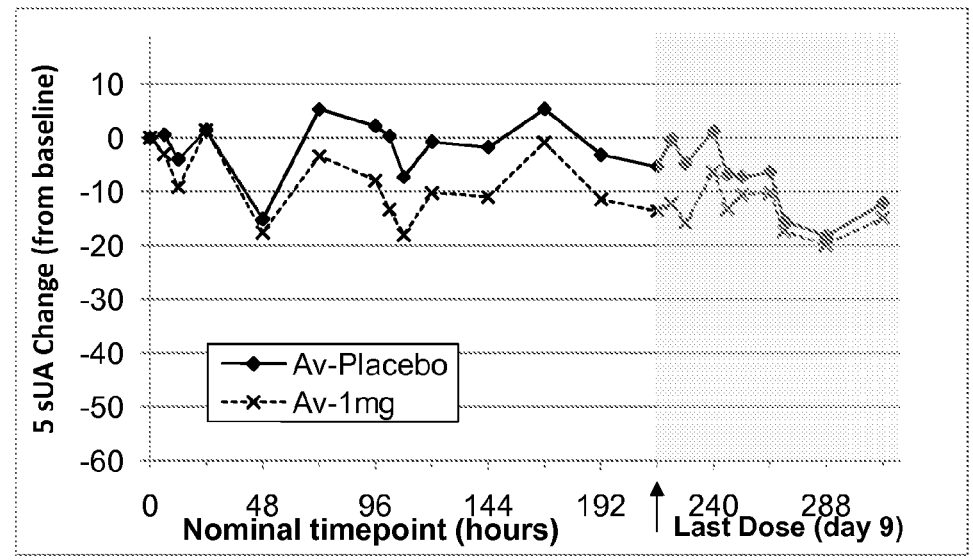
FIG. 7B shows the % serum uric acid change from baseline (mean placebo-subjects 1, 2 and 3; and mean active-subjects 4-12), measured at nominal timepoints (days 0-9—once daily dosing, plus days 10-13, post dosing) for twelve subjects in group 7 (1 mg, once daily for 10 days), as described in example 6A.

% sUA change (from baseline) by nominal timepoint (i.e. days 0-9—once daily dosing, plus days 10-13, post dosing) are shown in the table below, and presented in graphical form in FIG. 7B.

| | % sUA change (from baseline) | | | | | | | | | | | | | |
|---|---|---|---|---|---|---|---|---|---|---|---|---|---|---|
| | Subject Number | | | | | | | | | | | | Mean | Mean |
| Time | 1 | 2 | 3 | 4 | 5 | 6 | 7 | 8 | 9 | 10 | 11 | 12 | Placebo | (4-12) |
| 0 | 0 | 0 | 0 | 0 | 0 | 0 | 0 | 0 | 0 | 0 | 0 | 0 | 0 | 0 |
| 6 | 0.0 | −1.5 | 3.2 | −1.4 | −1.4 | 0.0 | 0.0 | −11.7 | −1.7 | −5.2 | −1.8 | −3.7 | 0.6 | −3.0 |
| 12 | −2.7 | −7.6 | −1.6 | −5.7 | −7.2 | −9.0 | −1.6 | −16.7 | −10.2 | −12.1 | −10.7 | −9.3 | −4.0 | −9.2 |
| 24 | 1.4 | 4.5 | −1.6 | 1.4 | −4.3 | 1.5 | 8.1 | −3.3 | 1.7 | 0.0 | 5.4 | 1.9 | 1.4 | 1.4 |
| 48 | −4.1 | −12.1 | −29.0 | −14.3 | −15.9 | −19.4 | −11.3 | −21.7 | −16.9 | −12.1 | −35.7 | −11.1 | −15.1 | −17.6 |
| 72 | 8.2 | 3.0 | 4.8 | 0.0 | −4.3 | −7.5 | 0.0 | −8.3 | 0.0 | −8.6 | 0.0 | −1.9 | 5.3 | −3.4 |
| 96 | 8.2 | −1.5 | 0.0 | −4.3 | −2.9 | −9.0 | −3.2 | −16.7 | −6.8 | −13.8 | −8.9 | −5.6 | 2.2 | −7.9 |
| 102 | 5.5 | −4.5 | 0.0 | −11.4 | −10.1 | −11.9 | −8.1 | −23.3 | −8.5 | −24.1 | −12.5 | −9.3 | 0.3 | −13.2 |
| 108 | 0.0 | −10.6 | −11.3 | −12.9 | −14.5 | −19.4 | −9.7 | −28.3 | −15.3 | −29.3 | −21.4 | −11.1 | −7.3 | −18.0 |
| 120 | 5.5 | −6.1 | −1.6 | −5.7 | −10.1 | −7.5 | −6.5 | −16.7 | −5.1 | −20.7 | −10.7 | −9.3 | −0.7 | −10.3 |
| 144 | 4.1 | −4.5 | −4.8 | −7.1 | −10.1 | −9.0 | −6.5 | −16.7 | −6.8 | −20.7 | −10.7 | −11.1 | −1.7 | −11.0 |
| 168 | 9.6 | 0.0 | 6.5 | 2.9 | −1.4 | −6.0 | 4.8 | −10.0 | 5.1 | −10.3 | 3.6 | 3.7 | 5.4 | −0.8 |
| 192 | 1.4 | −7.6 | −3.2 | −7.1 | −11.6 | −11.9 | −9.7 | −15.0 | −6.8 | −20.7 | −10.7 | −9.3 | −3.1 | −11.4 |
| 216 | 2.7 | −9.1 | −9.7 | −12.9 | −15.9 | −20.9 | −9.7 | −18.3 | 0.0 | −19.0 | −12.5 | −13.0 | −5.4 | −13.6 |
| 222 | 5.5 | −4.5 | −1.6 | −10.0 | −14.5 | −13.4 | −12.9 | −16.7 | −6.8 | −19.0 | −7.1 | −9.3 | −0.2 | −12.2 |
| 228 | 1.4 | −7.6 | −8.1 | −11.4 | −18.8 | −17.9 | −14.5 | −20.0 | −8.5 | −25.9 | −14.3 | −9.3 | −4.8 | −15.6 |
| 240 | 6.8 | 1.5 | −4.8 | −1.4 | −10.1 | −7.5 | −4.8 | −13.3 | 1.7 | −17.2 | −1.8 | −1.9 | 1.2 | −6.3 |
| 246 | 0.0 | −7.6 | −12.9 | −8.6 | −15.9 | −16.4 | −8.1 | −15.0 | −6.8 | −24.1 | −14.3 | −9.3 | −6.8 | −13.2 |
| 252 | 0.0 | −12.1 | −9.7 | −1.4 | −11.6 | −11.9 | −4.8 | −16.7 | −8.5 | −22.4 | −10.7 | −7.4 | −7.3 | −10.6 |
| 264 | 2.7 | −12.1 | −9.7 | −8.6 | −10.1 | −10.4 | −8.1 | −15.0 | −3.4 | −22.4 | −8.9 | −5.6 | −6.4 | −10.3 |
| 270 | −5.5 | −22.7 | −17.7 | −14.3 | −14.5 | −19.4 | −14.5 | −21.7 | −13.6 | −29.3 | −17.9 | −11.1 | −15.3 | −17.4 |
| 288 | −9.6 | −25.8 | −19.4 | −14.3 | −15.9 | −19.4 | −16.1 | −26.7 | −16.9 | −32.8 | −19.6 | −16.7 | −18.3 | −19.8 |
| 312 | −5.5 | −18.2 | −12.9 | −11.4 | −11.6 | −16.4 | −12.9 | −18.3 | −8.5 | −24.1 | −16.1 | −14.8 | −12.2 | −14.9 |

Timepoint in bold = dosing timepoints
Timepoints 222 and greater = post dosing

Example 6B: Multi-Dose Clinical Trial Results for Group 8

2-((3-(4-cyanonaphthalen-1-yl)pyridin-4-yl)thio)-2-methylpropanoic acid was evaluated according to the clinical trial described above in Example 5.

Results for ten subjects in group 8, receiving 5 mg active or placebo, once daily for 10 days, are shown below. Subjects 1, 2 and 3 received placebo; subjects 4-10 received active.

Figure 8A:
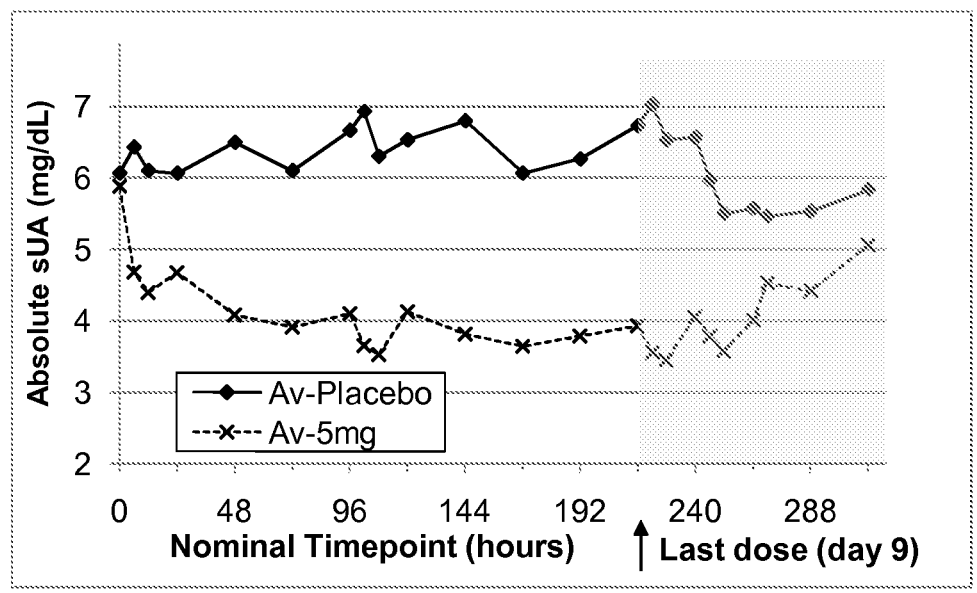
FIG. 8A shows the absolute serum uric acid concentrations (mg/dL; mean placebo-subjects 1, 2 and 3; and mean active-subjects 4-10), measured at nominal timepoints (days 0-9—once daily dosing, plus days 10-13, post dosing) for ten subjects in group 8 (5 mg, once daily for 10 days), as described in example 6B.

Absolute sUA concentrations (mg/dL) by nominal timepoint (i.e. days 0-9—once daily dosing, plus days 10-13, post dosing) are shown in the table below, and presented in graphical form in FIG. 8A.

| | Absolute sUA concentration (mg/dL) | | | | | | | | | | | |
|---|---|---|---|---|---|---|---|---|---|---|---|---|
| | Subject Number | | | | | | | | | | Mean | Mean |
| Time | 1 | 2 | 3 | 4 | 5 | 6 | 7 | 8 | 9 | 10 | Placebo | (4-10) |
| 0 | 6.5 | 6.3 | 5.4 | 6.5 | 6.5 | 6.0 | 5.8 | 5.6 | 5.5 | 5.3 | 6.1 | 5.9 |
| 6 | 6.9 | 6.6 | 5.8 | 5.3 | 5.3 | 4.8 | 4.8 | 4.3 | 3.8 | 4.5 | 6.4 | 4.7 |
| 12 | 6.7 | 6.2 | 5.4 | 5.2 | 5.3 | 4.5 | 4.6 | 3.9 | 3.3 | 4.0 | 6.1 | 4.4 |
| 24 | 6.7 | 6.3 | 5.2 | 5.3 | 5.6 | 5.0 | 5.4 | 4.2 | 3.4 | 3.8 | 6.1 | 4.7 |
| 48 | 7.4 | 6.5 | 5.6 | 5.2 | 4.1 | 4.4 | 5.1 | 3.7 | 3.1 | 3.0 | 6.5 | 4.1 |
| 72 | 7.1 | 5.9 | 5.3 | 4.5 | 4.2 | 4.3 | 4.7 | 3.5 | 3.0 | 3.2 | 6.1 | 3.9 |
| 96 | 8.0 | 6.3 | 5.7 | 4.6 | 4.3 | 4.2 | 4.8 | 3.7 | 3.5 | 3.6 | 6.7 | 4.1 |
| 102 | 8.0 | 6.8 | 6.0 | 4.1 | 3.7 | 3.8 | 4.2 | 3.1 | 3.0 | 3.7 | 6.9 | 3.7 |
| 108 | 7.2 | 6.2 | 5.5 | 4.4 | 3.8 | 3.4 | 4.0 | 2.9 | 2.8 | 3.4 | 6.3 | 3.5 |
| 120 | 7.4 | 6.6 | 5.6 | 4.9 | 4.4 | 4.3 | 4.6 | 3.9 | 3.1 | 3.7 | 6.5 | 4.1 |
| 144 | 8.0 | 6.3 | 6.1 | 4.4 | 4.0 | 3.7 | 4.4 | 3.6 | 3.3 | 3.3 | 6.8 | 3.8 |
| 168 | 6.8 | 5.9 | 5.5 | 4.1 | 3.6 | 3.7 | 4.4 | 3.5 | 3.3 | 2.9 | 6.1 | 3.6 |
| 192 | 7.3 | 6.0 | 5.5 | 4.4 | 3.8 | 3.6 | 4.8 | 3.6 | 3.1 | 3.2 | 6.3 | 3.8 |
| 216 | 7.5 | 6.1 | 6.6 | 4.4 | 4.4 | 3.9 | 4.4 | 3.3 | 4.1 | 3.0 | 6.7 | 3.9 |
| 222 | 7.6 | 6.7 | 6.8 | 4.0 | 3.9 | 3.7 | 3.9 | 3.1 | 3.2 | 3.1 | 7.0 | 3.6 |
| 228 | 7.1 | 6.2 | 6.3 | 4.1 | 3.9 | 3.4 | 3.7 | 3.1 | 3.2 | 2.8 | 6.5 | 3.5 |
| 240 | 6.9 | 6.4 | 6.4 | 4.7 | 4.5 | 4.0 | 4.3 | 4.1 | 3.6 | 3.2 | 6.6 | 4.1 |
| 246 | 6.3 | 5.7 | 5.9 | 4.4 | 4.0 | 3.8 | 4.1 | 3.9 | 3.3 | 3.0 | 6.0 | 3.8 |
| 252 | 5.8 | 5.3 | 5.4 | 4.2 | 3.7 | 3.3 | 4.0 | 3.8 | 3.2 | 2.9 | 5.5 | 3.6 |
| 264 | 5.7 | 5.3 | 5.7 | 4.4 | 4.0 | 4.0 | 4.2 | 4.1 | 4.0 | 3.3 | 5.6 | 4.0 |
| 270 | 5.6 | 5.3 | 5.5 | 5.0 | 4.4 | 4.5 | 5.0 | 4.7 | 4.0 | 4.1 | 5.5 | 4.5 |
| 288 | 5.7 | 5.4 | 5.5 | 4.9 | 4.3 | 4.1 | 4.8 | 4.8 | 4.2 | 3.8 | 5.5 | 4.4 |
| 312 | 5.6 | 6.1 | 5.8 | 5.6 | 4.7 | 4.9 | 5.5 | 5.2 | 4.9 | 4.6 | 5.8 | 5.1 |

Timepoint in bold = dosing timepoints
Timepoints 222 and greater = post dosing

Figure 8B:
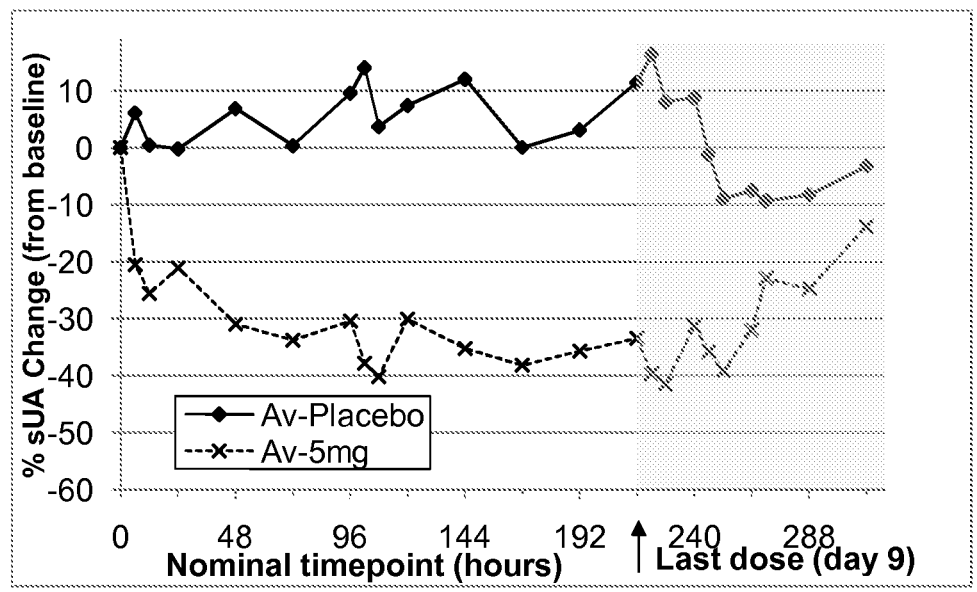
FIG. 8B shows the % serum uric acid change from baseline (mean placebo-subjects 1, 2 and 3; and mean active-subjects 4-10), measured at nominal timepoints (days 0-9—once daily dosing, plus days 10-13, post dosing) for ten subjects in group 8 (1 mg, once daily for 10 days), as described in example 6B.

% sUA change (from baseline) by nominal timepoint (i.e. days 0-9—once daily dosing, plus days 10-13, post dosing) are shown in the table below, and presented in graphical form in FIG. 8B.

| | % sUA change (from baseline) | | | | | | | | | | | |
|---|---|---|---|---|---|---|---|---|---|---|---|---|
| | Subject Number | | | | | | | | | | Mean | Mean |
| Time | 1 | 2 | 3 | 4 | 5 | 6 | 7 | 8 | 9 | 10 | Placebo | (4-12) |
| 0 | 0 | 0 | 0 | 0 | 0 | 0 | 0 | 0 | 0 | 0 | 0 | 0 |
| 6 | 6.2 | 4.8 | 7.4 | −18.5 | −18.5 | −20.0 | −17.2 | −23.2 | −30.9 | −15.1 | 6.1 | −20.5 |
| 12 | 3.1 | −1.6 | 0.0 | −20.0 | −18.5 | −25.0 | −20.7 | −30.4 | −40.0 | −24.5 | 0.5 | −25.6 |
| 24 | 3.1 | 0.0 | −3.7 | −18.5 | −13.8 | −16.7 | −6.9 | −25.0 | −38.2 | −28.3 | −0.2 | −21.1 |
| 48 | 13.8 | 3.2 | 3.7 | −20.0 | −36.9 | −26.7 | −12.1 | −33.9 | −43.6 | −43.4 | 6.9 | −30.9 |
| 72 | 9.2 | −6.3 | −1.9 | −30.8 | −35.4 | −28.3 | −19.0 | −37.5 | −45.5 | −39.6 | 0.3 | −33.7 |
| 96 | 23.1 | 0.0 | 5.6 | −29.2 | −33.8 | −30.0 | −17.2 | −33.9 | −36.4 | −32.1 | 9.6 | −30.4 |
| 102 | 23.1 | 7.9 | 11.1 | −36.9 | −43.1 | −36.7 | −27.6 | −44.6 | −45.5 | −30.2 | 14.0 | −37.8 |
| 108 | 10.8 | −1.6 | 1.9 | −32.3 | −41.5 | −43.3 | −31.0 | −48.2 | −49.1 | −35.8 | 3.7 | −40.2 |
| 120 | 13.8 | 4.8 | 3.7 | −24.6 | −32.3 | −28.3 | −20.7 | −30.4 | −43.6 | −30.2 | 7.4 | −30 |
| 144 | 23.1 | 0.0 | 13.0 | −32.3 | −38.5 | −38.3 | −24.1 | −35.7 | −40.0 | −37.7 | 12.0 | −35.2 |
| 168 | 4.6 | −6.3 | 1.9 | −36.9 | −44.6 | −38.3 | −24.1 | −37.5 | −40.0 | −45.3 | 0.1 | −38.1 |
| 192 | 12.3 | −4.8 | 1.9 | −32.3 | −41.5 | −40.0 | −17.2 | −35.7 | −43.6 | −39.6 | 3.1 | −35.7 |
| 216 | 15.4 | −3.2 | 22.2 | −32.3 | −32.3 | −35.0 | −24.1 | −41.1 | −25.5 | −43.4 | 11.5 | −33.4 |
| 222 | 16.9 | 6.3 | 25.9 | −38.5 | −40.0 | −38.3 | −32.8 | −44.6 | −41.8 | −41.5 | 16.4 | −39.6 |
| 228 | 9.2 | −1.6 | 16.7 | −36.9 | −40.0 | −43.3 | −36.2 | −44.6 | −41.8 | −47.2 | 8.1 | −41.4 |
| 240 | 6.2 | 1.6 | 18.5 | −27.7 | −30.8 | −33.3 | −25.9 | −26.8 | −34.5 | −39.6 | 8.8 | −31.2 |

-continued

| | % sUA change (from baseline) | | | | | | | | | | | |
|---|---|---|---|---|---|---|---|---|---|---|---|---|
| | Subject Number | | | | | | | | | | Mean | Mean |
| Time | 1 | 2 | 3 | 4 | 5 | 6 | 7 | 8 | 9 | 10 | Placebo | (4-12) |
| 246 | −3.1 | −9.5 | 9.3 | −32.3 | −38.5 | −36.7 | −29.3 | −30.4 | −40.0 | −43.4 | −1.1 | −35.8 |
| 252 | −10.8 | −15.9 | 0.0 | −35.4 | −43.1 | −45.0 | −31.0 | −32.1 | −41.8 | −45.3 | −8.9 | −39.1 |
| 264 | −12.3 | −15.9 | 5.6 | −32.3 | −38.5 | −33.3 | −27.6 | −26.8 | −27.3 | −37.7 | −7.5 | −31.9 |
| 270 | −13.8 | −15.9 | 1.9 | −23.1 | −32.3 | −25.0 | −13.8 | −16.1 | −27.3 | −22.6 | −9.3 | −22.9 |
| 288 | −12.3 | −14.3 | 1.9 | −24.6 | −33.8 | −31.7 | −17.2 | −14.3 | −23.6 | −28.3 | −8.2 | −24.8 |
| 312 | −13.8 | −3.2 | 7.4 | −13.8 | −27.7 | −18.3 | −5.2 | −7.1 | −10.9 | −13.2 | −3.2 | −13.7 |

Timepoint in bold = dosing timepoints
Timepoints 222 and greater = post dosing

Example 6C: Multi-Dose Clinical Trial Results for Group 9

2-((3-(4-cyanonaphthalen-1-yl)pyridin-4-yl)thio)-2-methylpropanoic acid was evaluated according to the clinical trial described above in Example 5.

Results for eleven subjects in group 9, receiving 10 mg active or placebo, once daily for 10 days, are shown below. Subjects 1 and 2 received placebo; subjects 3-11 received active.

Figure 9A:
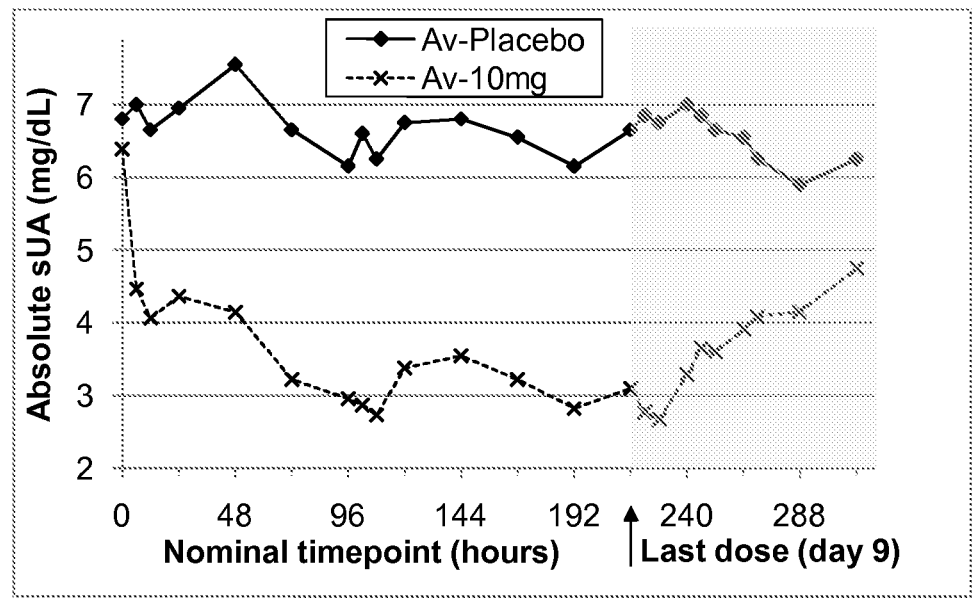
FIG. 9A shows the absolute serum uric acid concentrations (mg/dL; mean placebo-subjects 1, 2 and 3; and mean active-subjects 4-11), measured at nominal timepoints (days 0-9—once daily dosing, plus days 10-13, post dosing) for eleven subjects in group 9 (10 mg, once daily for 10 days), as described in example 6C.

Absolute sUA concentrations (mg/dL) by nominal timepoint (i.e. days 0-9—once daily dosing, plus days 10-13, post dosing) are shown in the table below, and presented in graphical form in FIG. 9A.

| | Absolute sUA concentration (mg/dL) | | | | | | | | | | | | |
|---|---|---|---|---|---|---|---|---|---|---|---|---|---|
| | Subject Number | | | | | | | | | | | Mean | Mean |
| Time | 1 | 2 | 3 | 4 | 5 | 6 | 7 | 8 | 9 | 10 | 11 | Placebo | (3-11) |
| 0 | 7.8 | 5.8 | 8.0 | 7.3 | 6.8 | 6.6 | 6.4 | 6.2 | 5.6 | 5.4 | 5.2 | 6.8 | 6.4 |
| 6 | 8.0 | 6.0 | 6.2 | 5.2 | 4.4 | 4.5 | 4.1 | 4.2 | 4.1 | 4.0 | 3.5 | 7.0 | 4.5 |
| 12 | 7.5 | 5.8 | 6.5 | 4.7 | 4.1 | 3.2 | 3.5 | 4.2 | 3.6 | 3.8 | 3.0 | 6.7 | 4.1 |
| 24 | 7.8 | 6.1 | 6.8 | 5.2 | 4.0 | 3.3 | 4.2 | 4.2 | 4.8 | 3.6 | 3.2 | 7.0 | 4.4 |
| 48 | 8.3 | 6.8 | 5.5 | 5.1 | 3.3 | 3.6 | 4.4 | 4.0 | 4.7 | 3.4 | 3.3 | 7.6 | 4.1 |
| 72 | 7.3 | 6.0 | 4.4 | 4.0 | 2.7 | 3.0 | 3.6 | 3.0 | 3.5 | 2.6 | 2.2 | 6.7 | 3.2 |
| 96 | 6.7 | 5.6 | 3.9 | 3.7 | 2.3 | 2.9 | 3.1 | 2.8 | 3.2 | 2.5 | 2.2 | 6.2 | 3.0 |
| 102 | 7.0 | 6.2 | 3.9 | 3.1 | 2.4 | 3.0 | 3.4 | 2.7 | 2.8 | 2.7 | 1.8 | 6.6 | 2.9 |
| 108 | 6.6 | 5.9 | 3.9 | 3.0 | 2.1 | 2.3 | 3.1 | 2.8 | 2.8 | 2.7 | 1.9 | 6.3 | 2.7 |
| 120 | 7.3 | 6.2 | 4.6 | 3.8 | 2.7 | 2.9 | 3.8 | 3.6 | 3.6 | 2.9 | 2.5 | 6.8 | 3.4 |
| 144 | 7.6 | 6.0 | 4.8 | 3.5 | 2.8 | 3.1 | 3.8 | 4.7 | 3.6 | 3.0 | 2.6 | 6.8 | 3.5 |
| 168 | 7.2 | 5.9 | 4.9 | 3.2 | 2.4 | 2.9 | 3.3 | 4.1 | 3.3 | 2.5 | 2.4 | 6.6 | 3.2 |
| 192 | 6.8 | 5.5 | 4.2 | 3.0 | 2.0 | 2.3 | 3.2 | 3.1 | 3.1 | 2.3 | 2.2 | 6.2 | 2.8 |
| 216 | 7.3 | 6.0 | 4.5 | 3.2 | 2.4 | 2.9 | NA | 3.2 | 3.5 | 2.6 | 2.5 | 6.7 | 3.1 |
| 222 | 7.6 | 6.1 | 3.9 | 2.6 | 2.1 | 2.6 | NA | 2.7 | 3.4 | 2.6 | 2.3 | 6.9 | 2.8 |
| 228 | 7.4 | 6.1 | 3.7 | 2.4 | 2.1 | 2.3 | 2.9 | 2.5 | 3.1 | 2.7 | 2.3 | 6.8 | 2.7 |
| 240 | 7.8 | 6.2 | 4.9 | 3.6 | 2.7 | 2.5 | 4.1 | 3.1 | 3.6 | 2.4 | 2.7 | 7.0 | 3.3 |
| 246 | 7.6 | 6.1 | 5.4 | 3.6 | 3.2 | 3.2 | 4.3 | 3.6 | 4.0 | 2.5 | 3.1 | 6.9 | 3.7 |
| 252 | 7.3 | 6.0 | 5.3 | 3.3 | 3.1 | 3.1 | 4.4 | 3.9 | 3.7 | 2.7 | 2.9 | 6.7 | 3.6 |
| 264 | 7.1 | 6.0 | 5.7 | 3.6 | 3.4 | 3.7 | 4.9 | 4.2 | 3.8 | 2.7 | 3.2 | 6.6 | 3.9 |
| 270 | 6.7 | 5.8 | 5.7 | 3.8 | 3.5 | 4.2 | 5.1 | 4.6 | 4.0 | 2.7 | 3.2 | 6.3 | 4.1 |
| 288 | 6.4 | 5.4 | 5.7 | 4.0 | 3.7 | 4.4 | 4.8 | 4.8 | 3.9 | 2.8 | 3.3 | 5.9 | 4.2 |
| 312 | 6.8 | 5.7 | 6.5 | 4.8 | 4.3 | 5.0 | 5.5 | 5.2 | 4.3 | 3.3 | 3.8 | 6.3 | 4.7 |

Timepoint in bold = dosing timepoints
Timepoints 222 and greater = post dosing

Figure 9B:
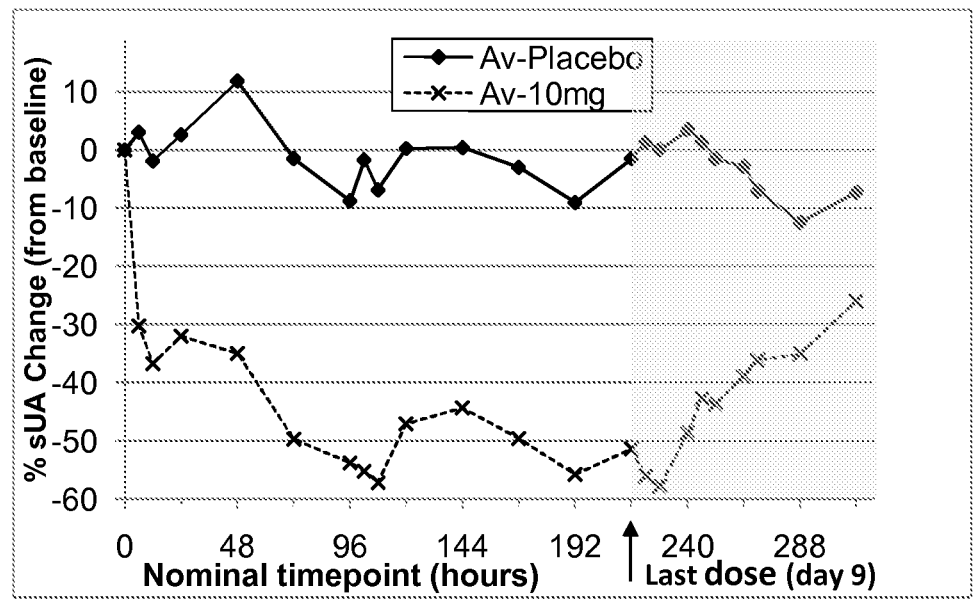
FIG. 9B shows the % serum uric acid change from baseline (mean placebo-subjects 1, 2 and 3; and mean active-subjects 4-11), measured at nominal timepoints (days 0-9—once daily dosing, plus days 10-13, post dosing) for eleven subjects in group 9 (10 mg, once daily for 10 days), as described in example 6C.

% sUA change (from baseline) by nominal timepoint (i.e. days 0-9—once daily dosing, plus days 10-13, post dosing) are shown in the table below, and presented in graphical form in FIG. 9B.

| | % sUA change (from baseline) | | | | | | | | | | | | |
|---|---|---|---|---|---|---|---|---|---|---|---|---|---|
| | Subject Number | | | | | | | | | | | Mean | Mean |
| Time | 1 | 2 | 3 | 4 | 5 | 6 | 7 | 8 | 9 | 10 | 11 | Placebo | (3-11) |
| 0 | 0 | 0 | 0 | 0 | 0 | 0 | 0 | 0 | 0 | 0 | 0 | 0 | 0 |
| 6 | 2.6 | 3.4 | −22.5 | −28.8 | −31.8 | −35.9 | −35.3 | −32.3 | −26.8 | −25.9 | −32.7 | 3.0 | −30.2 |
| 12 | −3.8 | 0.0 | −18.8 | −35.6 | −39.7 | −51.5 | −45.3 | −35.7 | −32.3 | −29.6 | −42.3 | −1.9 | −36.8 |
| 24 | 0.0 | 5.2 | −15.0 | −28.8 | −41.2 | −50.0 | −34.4 | −32.3 | −14.3 | −33.3 | −38.5 | 2.6 | −32.0 |
| 48 | 6.4 | 17.2 | −31.3 | −30.1 | −51.5 | −45.5 | −31.3 | −35.5 | −16.1 | −37.0 | −36.5 | 11.8 | −35.0 |
| 72 | −6.4 | 3.4 | −45.0 | −45.2 | −60.3 | −54.5 | −43.8 | −51.6 | −37.5 | −51.9 | −57.7 | −1.5 | −49.7 |
| 96 | −14.1 | −3.4 | −51.3 | −49.3 | −66.2 | −56.1 | −51.6 | −54.8 | −42.9 | −53.7 | −57.7 | −8.8 | −53.7 |
| 102 | −10.3 | 6.9 | −51.3 | −57.5 | −64.7 | −54.5 | −46.9 | −56.5 | −50.0 | −50.0 | −65.4 | −1.7 | −55.2 |
| 108 | −15.4 | 1.7 | −51.3 | −58.9 | −69.1 | −65.2 | −51.6 | −54.8 | −50.0 | −50.0 | −63.5 | −6.9 | −57.2 |
| 120 | −6.4 | 6.9 | −42.5 | −47.9 | −60.3 | −56.1 | −40.6 | −41.9 | −35.7 | −46.3 | −51.9 | 0.3 | −47.0 |
| 144 | −2.6 | 3.4 | −40.0 | −52.1 | −58.8 | −53.0 | −40.6 | −24.2 | −35.7 | −44.4 | −50.0 | 0.4 | −44.3 |
| 168 | −7.7 | 1.7 | −38.7 | −56.2 | −64.7 | −56.1 | −48.4 | −33.9 | −41.1 | −53.7 | −53.8 | −3.0 | −49.6 |
| 192 | −12.8 | −5.2 | −47.5 | −58.9 | −70.6 | −65.2 | −50.0 | −50.0 | −44.6 | −57.4 | −57.7 | −9.0 | −55.8 |
| 216 | −6.4 | 3.4 | −43.8 | −56.2 | −64.7 | −56.1 | NA | −48.4 | −37.5 | −51.9 | −51.9 | −1.5 | −51.3 |
| 222 | −2.6 | 5.2 | −51.3 | −64.4 | −69.1 | −60.6 | NA | −56.5 | −39.3 | −51.9 | −55.8 | 1.3 | −56.1 |
| 228 | −5.1 | 5.2 | −53.8 | −67.1 | −69.1 | −65.2 | −54.7 | −59.7 | −44.6 | −55.0 | −57.8 | 0.1 | −57.8 |
| 240 | 0.0 | 6.9 | −38.7 | −50.7 | −60.3 | −62.1 | −35.9 | −50.0 | −35.7 | −55.6 | −48.1 | 3.5 | −48.6 |
| 246 | −2.6 | 5.2 | −32.5 | −50.7 | −52.9 | −51.5 | −32.8 | −41.9 | −28.6 | −53.7 | −40.4 | 1.3 | −42.8 |
| 252 | −6.4 | 3.4 | −33.8 | −54.8 | −54.4 | −53.0 | −31.3 | −37.1 | −33.9 | −50.0 | −44.2 | −1.5 | −43.6 |
| 264 | −9.0 | 3.4 | −28.8 | −50.7 | −50.0 | −43.9 | −23.4 | −32.3 | −32.1 | −50.0 | −38.5 | −2.8 | −38.9 |
| 270 | −14.1 | 0.0 | −28.8 | −47.9 | −48.5 | −36.4 | −20.3 | −25.8 | −28.6 | −50.0 | −38.5 | −7.1 | −36.1 |
| 288 | −17.9 | −6.9 | −28.8 | −45.2 | −45.6 | −33.3 | −25.0 | −22.6 | −30.4 | −48.1 | −36.5 | −12.4 | −35.1 |
| 312 | −12.8 | −1.7 | −18.8 | −34.2 | −36.8 | −24.2 | −14.1 | −16.1 | −23.2 | −38.9 | −26.9 | −7.3 | −25.9 |

Timepoint in bold = dosing timepoints
Timepoints 222 and greater = post dosing

Figure 10A:
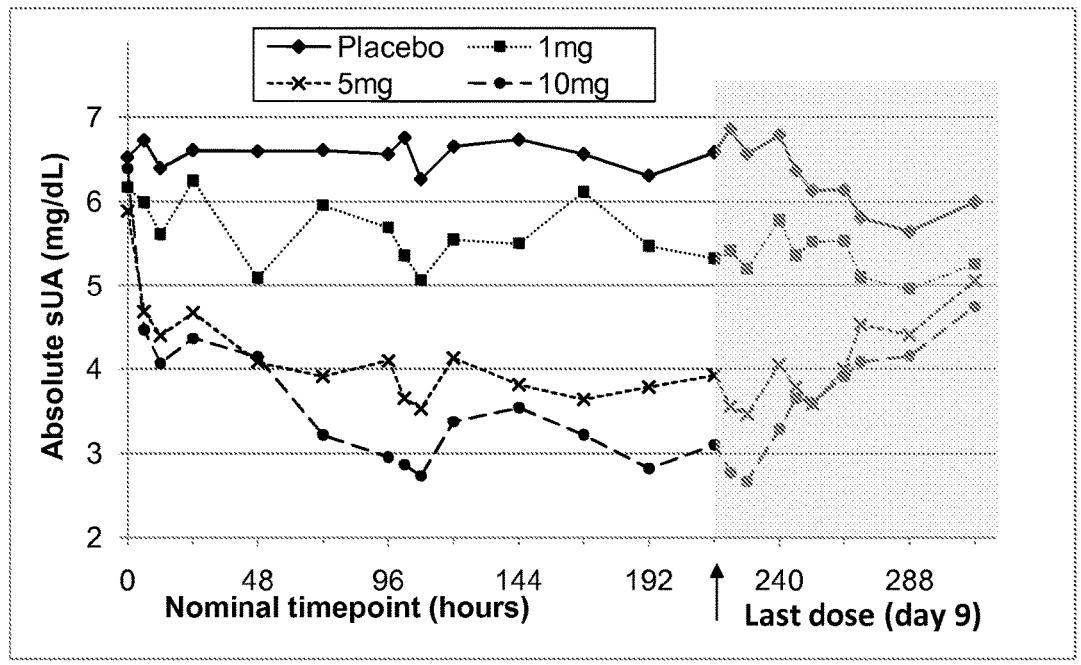
FIG. 10A shows the mean absolute serum uric acid concentrations (mg/dL), measured at nominal timepoints (days 0-9—once daily dosing, plus days 10-13, post dosing) for groups 7, 8 and 9 (1 mg, 5 mg and 10 mg respectively, once daily for 10 days, placebo groups pooled), as described in example 6.
Figure 10B:
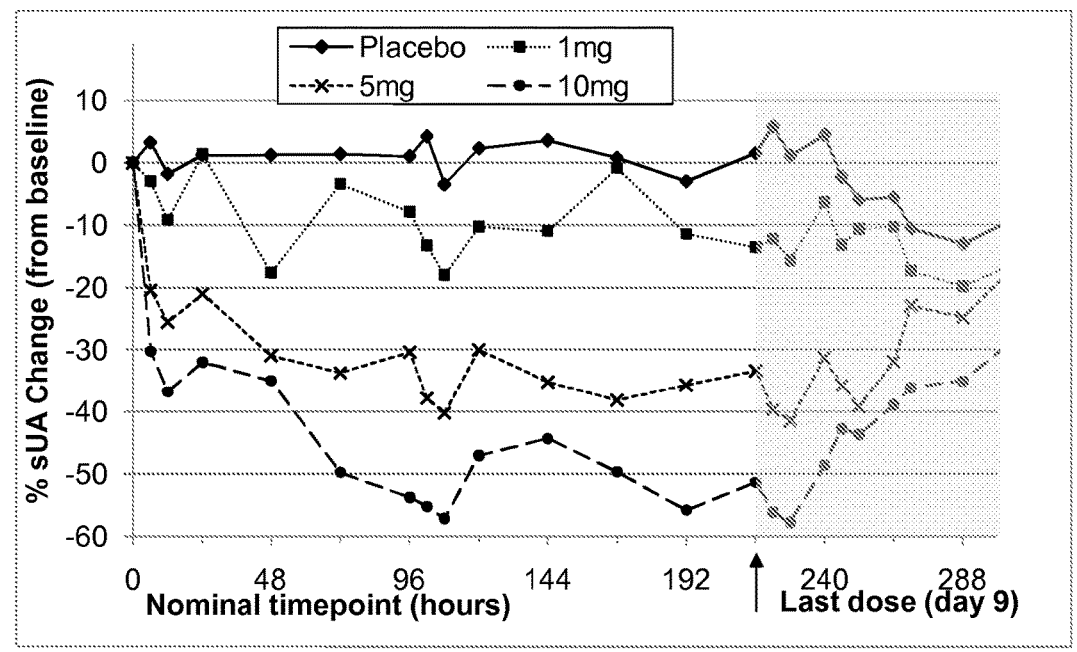
FIG. 10B shows the mean % serum uric acid change from baseline measured at nominal timepoints (days 0-9—once daily dosing, plus days 10-13, post dosing) for groups 7, 8 and 9 (1 mg, 5 mg and 10 mg respectively, once daily for 10 days, placebo groups pooled), as described in example 6.

Absolute sUA and % sUA change by nominal timepoint (i.e. days 0-9—once daily dosing, plus days 10-13, post dosing) for groups 7, 8 and 9 (1 mg, 5 mg and 10 mg, all fasted; placebo groups pooled) are presented in graphical form in FIGS. 10A and 10B respectively.

The examples and embodiments described herein are for illustrative purposes only and various modifications or changes suggested to individuals skilled in the art are to be included within the spirit and purview of this application and scope of the appended claims.

What is claimed is:

1. A method for reducing serum uric acid levels in a human, comprising administering to the human between about 2 mg and less than 10 mg per day of 2-((3-(4-cyanonaphthalen-1-yl)pyridin-4-yl)thio)-2-methylpropanoic acid, or a pharmaceutically acceptable salt thereof.

2. The method of claim 1, wherein about 4 mg per day of 2-((3-(4-cyanonaphthalen-1-yl)pyridin-4-yl)thio)-2-methylpropanoic acid, or a pharmaceutically acceptable salt, is administered to the human.

3. The method of claim 1, wherein about 2 mg per day of 2-((3-(4-cyanonaphthalen-1-yl)pyridin-4-yl)thio)-2-methylpropanoic acid, or a pharmaceutically acceptable salt, is administered to the human.

4. The method of claim 1, wherein about 5 mg per day of 2-((3-(4-cyanonaphthalen-1-yl)pyridin-4-yl)thio)-2-methylpropanoic acid, or a pharmaceutically acceptable salt, is administered to the human.

5. The method of claim 1, wherein between about 2 mg and about 5 mg per day of 2-((3-(4-cyanonaphthalen-1-yl)pyridin-4-yl)thio)-2-methylpropanoic acid, or a pharmaceutically acceptable salt, is administered to the human.

6. The method of claim 1, wherein 24 hours after administration of 2-((3-(4-cyanonaphthalen-1-yl)pyridin-4-yl)thio)-2-methylpropanoic acid, the serum uric acid levels are reduced by at least 15% from baseline.

7. The method of claim 1, wherein 24 hours after administration of 2-((3-(4-cyanonaphthalen-1-yl)pyridin-4-yl)thio)-2-methylpropanoic acid, the serum uric acid levels are reduced by at least 20% from baseline.

8. A method for treating a condition in a human comprising administering to the human between about 2 mg and less than 10 mg per day of 2-((3-4-cyanonaphthalen-1-yl)pyridin-4-yl)thio)-2-methylpropanoic acid, or a pharmaceutically acceptable salt thereof; wherein the condition is selected from the group consisting of gout, a recurrent gout attack, gouty arthritis, hyperuricemia, hypertension, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis, sarcoidosis, hypoxanthine-guanine phosphoribosyltransferase (HPRT) deficiency or a combination thereof; and wherein serum uric acid levels in the human are reduced.

9. The method of claim 8, wherein the condition is gout.

10. The method of claim 1, wherein a second agent effective for the treatment of the gout is administered to the human.

11. The method of claim 10, wherein the second agent is a URAT 1 inhibitor, a xanthine oxidase inhibitor, a xanthine dehydrogenase, a xanthine oxidoreductase inhibitor, or combinations thereof.

12. The method of claim 11, wherein the URAT 1 inhibitor is 2-((5-bromo-4-(4-cyclopropyl-1-naphthalenyl)-4H-1,2,4-triazol-3-yl)thio)acetic acid, or a pharmaceutically acceptable salt thereof.

13. The method of claim 11, wherein the xanthine oxidase inhibitor is allopurinol or febuxostat.

* * * * *